(12) United States Patent
De La Huerga

(10) Patent No.: US 7,013,298 B1
(45) Date of Patent: Mar. 14, 2006

(54) METHOD AND SYSTEM FOR AUTOMATED DATA STORAGE AND RETRIEVAL

(75) Inventor: Carlos De La Huerga, Milwaukee, WI (US)

(73) Assignee: HyperPhrase Technologies, LLC, Madison, WI (US)

(*) Notice: Subject to any disclaimer, the term of this patent is extended or adjusted under 35 U.S.C. 154(b) by 0 days.

(21) Appl. No.: 09/247,349

(22) Filed: May 3, 1999

Related U.S. Application Data

(63) Continuation-in-part of application No. 08/727,293, filed on Oct. 9, 1996, now Pat. No. 5,895,461, and a continuation-in-part of application No. 08/871,818, filed on Jun. 9, 1997, now Pat. No. 5,903,889.
(60) Provisional application No. 60/023,126, filed on Jul. 30, 1996, now Pat. No. 5,903,889.

(51) Int. Cl.
*G06F 17/30* (2006.01)
*G06F 17/60* (2006.01)
*G06F 15/16* (2006.01)

(52) U.S. Cl. ............................. 707/3; 707/10; 707/102; 707/104; 705/2; 705/3; 705/4; 709/217; 709/218

(58) Field of Classification Search ..................... 707/3, 707/4, 10, 102, 104; 705/4, 3; 709/217, 218
See application file for complete search history.

(56) References Cited

U.S. PATENT DOCUMENTS

| | | | |
|---|---|---|---|
| 4,332,009 A | 5/1982 | Gerson | |
| 4,384,288 A | 5/1983 | Walton | 340/825.34 |
| 4,575,621 A | 3/1986 | Dreifus | 235/380 |
| 4,864,501 A | 9/1989 | Kucera et al. | 364/419 |
| 4,878,175 A | 10/1989 | Norden-Paul et al. | |
| 4,887,212 A | 12/1989 | Zamora et al. | 364/419 |
| 4,994,966 A | 2/1991 | Hutchins | 364/419 |
| 5,204,947 A | 4/1993 | Bernstein et al. | |
| 5,233,513 A | 8/1993 | Doyle | |

(Continued)

FOREIGN PATENT DOCUMENTS

| | | |
|---|---|---|
| EP | 0 323 030 A2 | 5/1989 |
| EP | 0 234 831 B1 | 11/1992 |
| GB | 2154433 | 9/1985 |
| WO | WO01/33432 A1 | 5/2001 |
| WO | WO01/35714 A2 | 5/2001 |

OTHER PUBLICATIONS

A Pumped–Up Publishing Pro., Computer Shopper, Apr. 1997 v16 n4 p462, Susan Glinert.
Web Documents Without HTML, Computer Shopper, Apr. 1997 v16 n4 p412, Ben Goodman.
Acrobat, Common Ground Extend Reach Beyond Documetn Viewing, InfoWorld Apr. 21, 1997 v19 n16 p105(2), Patrick Marshall.
Publish To Paper and the Web, PC/Computing Dec. 1996 v9 n12 p130(1), Bob Weibel.
Microsoft Corporation, Microsoft Word 97, 4 Screen printouts, pp. 1–4, 1997.

*Primary Examiner*—Frantz Coby
(74) *Attorney, Agent, or Firm*—Quarles & Brady LLP

(57) ABSTRACT

A system and method for creating links between first records stored on a database and references to the first records within a second record, the system including a data reference list including keywords or phrases which may be used in the second record to reference the first records, the system also including address formats corresponding to each data reference which indicate the form of a first record address corresponding to the data reference, the system also including record rule sets for gleaning information from the second record for populating the address format, when a data reference is identified, the system identifying the corresponding address format, gleaning address information from the second record, forming the record address and linking the first record reference to the first record via the record address.

43 Claims, 30 Drawing Sheets

U.S. PATENT DOCUMENTS

| | | |
|---|---|---|
| 5,283,884 A | 2/1994 | Menon et al. |
| 5,291,399 A | 3/1994 | Chaco |
| 5,297,249 A | 3/1994 | Bernstein et al. |
| 5,319,711 A | 6/1994 | Servi .......................... 380/23 |
| 5,361,346 A | 11/1994 | Panesar et al. |
| 5,404,435 A | 4/1995 | Rosenbaum |
| 5,418,942 A | 5/1995 | Krawchuk et al. |
| 5,434,974 A | 7/1995 | Loucks et al. .............. 395/200 |
| 5,438,655 A | 8/1995 | Richichi et al. ............ 395/142 |
| 5,490,250 A | 2/1996 | Reschke et al. |
| 5,515,534 A | 5/1996 | Chuah et al. ............... 395/600 |
| 5,535,372 A | 7/1996 | Benhase et al. |
| 5,541,583 A | 7/1996 | Mandelbaum ......... 340/825.54 |
| 5,558,638 A | 9/1996 | Evers et al. |
| 5,560,005 A | 9/1996 | Hoover et al. |
| 5,581,460 A | 12/1996 | Kotake et al. |
| 5,603,025 A | 2/1997 | Tabb et al. |
| 5,608,900 A | 3/1997 | Dockter et al. |
| 5,629,981 A | 5/1997 | Nerlikar ...................... 380/25 |
| 5,659,676 A | 8/1997 | Redpath |
| 5,708,825 A * | 1/1998 | Sotomayor .................. 395/762 |
| 5,724,608 A | 3/1998 | Tohara |
| 5,740,252 A | 4/1998 | Minor et al. |
| 5,745,360 A | 4/1998 | Leone et al. |
| 5,745,908 A | 4/1998 | Anderson et al. ........... 707/513 |
| 5,754,857 A | 5/1998 | Gadol |
| 5,761,436 A | 6/1998 | Nielsen |
| 5,764,906 A | 6/1998 | Edelstein et al. ...... 395/200.49 |
| 5,781,900 A | 7/1998 | Shoji et al. |
| 5,790,856 A | 8/1998 | Lillich |
| 5,794,050 A | 8/1998 | Dahlgren et al. ........... 395/708 |
| 5,806,079 A | 9/1998 | Rivette et al. |
| 5,815,830 A * | 9/1998 | Anthony ........................ 707/6 |
| 5,819,092 A | 10/1998 | Ferguson et al. |
| 5,822,539 A * | 10/1998 | Van Hoff ............... 395/200.66 |
| 5,822,720 A | 10/1998 | Bookman et al. |
| 5,832,258 A | 11/1998 | Kiuchi et al. |
| 5,842,224 A | 11/1998 | Fenner |
| 5,860,073 A | 1/1999 | Ferrel et al. |
| 5,860,136 A | 1/1999 | Fenner |
| 5,862,325 A | 1/1999 | Reed et al. |
| 5,867,562 A | 2/1999 | Scherer |
| 5,867,821 A | 2/1999 | Ballantyne et al. |
| 5,875,446 A | 2/1999 | Brown et al. |
| 5,878,421 A | 3/1999 | Ferrel et al. |
| 5,884,302 A | 3/1999 | Ho ................................. 707/3 |
| 5,895,461 A | 4/1999 | de la Huerga et al. |
| 5,895,496 A | 4/1999 | James et al. |
| 5,903,889 A | 5/1999 | de la Huerga et al. |
| 5,905,866 A | 5/1999 | Nakabayashi et al. |
| 5,942,986 A | 8/1999 | Shabot et al. |
| 5,963,205 A | 10/1999 | Sotomayor |
| 5,963,950 A | 10/1999 | Nielsen et al. |
| 5,970,505 A | 10/1999 | Ebrahim |
| 5,974,413 A | 10/1999 | Beauregard et al. |
| 5,987,475 A | 11/1999 | Murai |
| 6,014,677 A | 1/2000 | Hayashi et al. ............. 707/501 |
| 6,031,537 A | 2/2000 | Hugh |
| 6,038,573 A | 3/2000 | Parks |
| 6,094,649 A | 7/2000 | Bowen et al. |
| 6,128,635 A * | 10/2000 | Ikeno .......................... 707/532 |
| 6,141,663 A | 10/2000 | Hunkins et al. |
| 6,151,624 A | 11/2000 | Teare et al. |
| 6,157,914 A | 12/2000 | Seto et al. |
| 6,178,434 B1 | 1/2001 | Saitoh |
| 6,188,751 B1 | 2/2001 | Scherer |
| 6,208,998 B1 | 3/2001 | Marcus |
| 6,230,283 B1 | 5/2001 | Gambino |
| 2002/0083183 A1 | 6/2002 | Pujare et al. |
| 2002/0159595 A1 | 10/2002 | Boudreqult et al. |
| 2003/0067472 A1 | 4/2003 | Radke et al. |

* cited by examiner

| Database Table | | | |
|---|---|---|---|
| Database 1 Register | Address(es) | File Format Instruction Table 1 | |
| ⋮ | | | |
| Database N Register | Address(es) | File Format Instruction Table N | |

130 — Database Table
134 — File Format Instruction Table 1
131 — Database N Register
132 — Address(es)

Figure 3A

| File Format Instruction Table | | | |
|---|---|---|---|
| Data Type 1 | Hypertext Cipher | URL Cipher | Special Instructions To Retrieve Data |
| ⋮ | | | |
| Data Type M | Hypertext Cipher | URL Cipher | Special Instructions To Retrieve Data |

134
136 — Data Type M
138 — Hypertext Cipher
140 — URL Cipher
142 — Special Instructions To Retrieve Data

Figure 3B

| Workstation Data Table |||
|---|---|---|
| Workstation 1 | Address | File Access Commands |
| ⋮ | | |
| Workstation N | Address | File Access Commands |

Figure 4A

| Workstation File Formatting Instruction Table |||
|---|---|---|
| Report 1 Name | File Name & Data Formatting Instructions | Workstation URL Cipher |
| ⋮ | | |
| Report M Name | File Name & Data Formatting Instructions | Workstation URL Cipher |

Figure 4B

```
400   <html>
      <body>

<font size=6>Charles F. Smith<br>
      font size=4> Medical records from 15-AUG-1998 to 23-AUG-1998<br>
      Community Hospital, Springfield<br><br>

404   <a href="demographics.html">Demographics</a><br>
      <a href="admission_report.html">Admission Report</a><br>
      <a href="/cardiology.html">Cardiology</a><br>
      <a href="/laboratory.html">Laboratory</a><br>
      <a href="/vital_signs.html">Vital Signs</a><br>
                                    •
                                    •
408                                 •
      <a href="discharge_report.html">Discharge Report</a><br>

</body>
      </html>
```

402 braces the link list.

Figure 6A

Charles F. Smith
Medical records from 15-AUG-1998 to 23-AUG-1998,
Community Hospital, Springfield 404 — Demographics
Admission Report
Cardiology
Vital Signs
•
•
408 — •
Discharge Report

412
```
<html>
<body>
DISCHARGE SUMMARY for Charles F. Smith<br><br>

Date of Admission: 15-AUG-98<br>
Date of Discharge: 17-AUG-98<br><br>

HISTORY OF PRESENT ILLNESS:<br>
Patient #1 is a 47-year-old male admitted for further evaluation of recent exertional
angina and abnormal exercise test.<br><br>
```

416
```
HOSPITAL COURSE:<br>
The patient was admitted to the Telemetry unit and underwent <a
href="charles_f_smith/cardiology/cath/1998-08-15/10:25/report.html">cardiac
catheterization on August 15, 1998</a>. Catheterization demonstrated normal
ventricular function without evidence for prior infarction. The coronary arteriogram
showed moderate stenosis throughout the mid and distal portions of the left anterior
descending artery and diagonal branch, as well as ● ● ●●
```

DISCHARGE SUMMARY for Charles F. Smith

Date of Admission: 15-AUG-98
Date of Discharge: 17-AUG-98

HISTORY OF PRESENT ILLNESS:
Patient #1 is a 47-year-old male admitted for further evaluation of recent
exertional angina and abnormal exercise test.

HOSPITAL COURSE:<br>
The patient was admitted to the Telemetry unit and underwent <u>catheterization on August 15, 1998</u>. Catheterization demonstrated normal ventricular function without evidence for prior infarction. The coronary arteriogram showed moderate stenosis throughout the mid and distal portions of the left anterior descending artery and diagonal branch, as well as ● ● ●●

Figure 7B

```
<html>
<body>

<font size=6>Charles F. Smith<br>
font size=4>Cardiology records from 15-AUG-1998 to 23-AUG-1998<br>
Community Hospital, Springfield<br><br>

<a href="/ecg/list.html">Ecg Reports</a><br>
<a href="cath/1998-08-15/10:25/report.html">Catheterization Procedure</a><br>
<a href="/stress/list.html">Stress Tests</a><br>
<a href="holter/1998-08-19/11:04/report.html">Holter</a><br>
            •
            •
            •
<a href=""nuclear/1998-08-20/14:54/report.html">Nuclear Scan</a><br>

</body>
</html>
```

Figure 8A

Charles F. Smith

Cardiology records from 15-AUG-1998 to 23-AUG-1998,
Community Hospital, Springfield <u>Ecg Reports</u>
<u>Catheterization Procedure</u>
<u>Stress Tests</u>
<u>Holter</u>
    •
    •
    •
<u>Nuclear Scan</u>

Figure 8B

```
424    <html>
       <body>

<font size=6>Charles F. Smith<br>
       font size=4>ECG records from 15-AUG-1998 to 23-AUG-1998<br>
       Community Hospital, Springfield<br><br>

<a href="ecg/1998-08-15/09:15/report.html">15-AUG-1998
       09:15</a><br>
       <a href="ecg/1998-08-15/16:40/report.html">15-AUG-1998
426    14:40</a><br>
       <a href="ecg/1998-08-17/11:03/report.html">17-AUG-1998
       11:03</a><br>
                                       •
       <a href="ecg/1998-08-19/10:25/report.html">19-AUG-1998
       09:15</a><br>
```

Figure 9A

118  Charles F. Smith
     Ecg records from 15-AUG-1998 to 23-AUG-1998,
     Community Hospital, Springfield

15-AUG-1998 09:15
     15-AUG-1998 14:40
     17-AUG-1998 11:03
     19-AUG-1998 09:15
426           •
              •
              •
     23-AUG-1998 08:14

Figure 9B

```
<html>

<body>
<img src="http://hww.st_mary.springfield/logo.gif"><br>

Catheterization Report for Charles F. Smith
<a href="http://hww.st_mary.springfield/demographics/complete/987654321/
15_AUG_1998/10:25/current.">Demographics</a><br><br>

Date of Procedure: 15-AUG-98 10:25<br><br>

RECOMMENDATIONS: Catheterization shows normal left ventricular function
with no evidence for prior injury. The left coronary system shows scattered and
moderately diffuse coronary disease consistent with the patient's history of

•
                                •
                                • clinically and show that ischemia is adequately controlled, then she will be followed
closely on medical therapy with follow-ups and repeat thallium evaluations.

<a href="http://hww.st_mary.springfield/cath/987654321/15_AUG_1996/10:25/
radiology.html">Radiology Catheterization Report </a><br>
<a href="http://hww.st_mary.springfield/cath/987654321/15_AUG_1996/10:25/
hemodynamic.html">Hemodynamic Catheterization Report </a><br>

</body>
</html>
```

Figure 14D

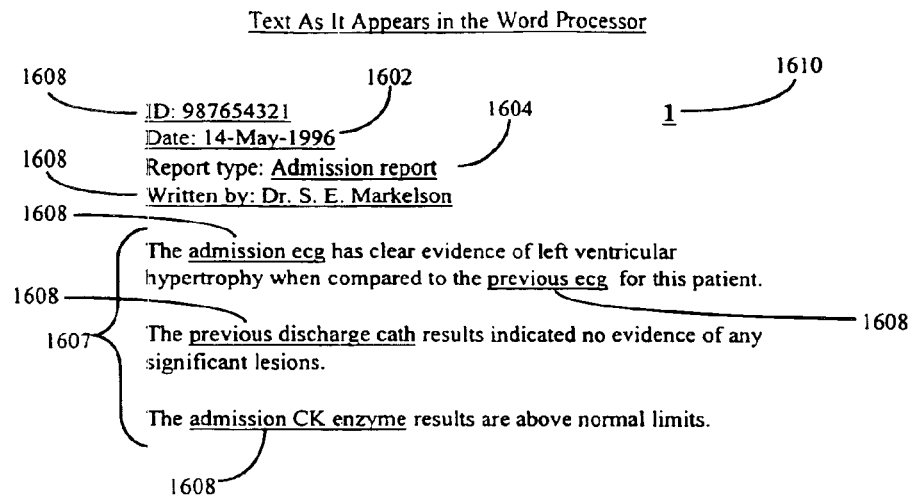

Text As It Appears in the Word Processor

Figure 17

Text after Being Converted to HTML with Hypertext Links Added

```
<html>
<body>
<a href= "http://hww.st_mary.springfield/demographics/987654321/14_May_1996">
ID: 987654321</a><br>
Date: 14-May-1996<br>
Report type: Admission report
Written by:  <a href="http://hww.st_mary.springfield/staff_directory/S._E._Markelson">
Dr. S. E. Markelson</a><br>
<br>
The <a href="http://hww.st_mary.springfield/ecg/987654321/14_May_1996/00:00/admit">
admission ecg </a> has clear evidence of left ventricular hypertrophy when compared to the
    <a href="http://hww.st_mary.springfield/ecg/987654321/14_May_1996/00:00/current">
previous ecg </a> for this patient.<br>
<br>
The
<a
href="http://hww.st_mary.springfield/cath/987654321/14_May_1996/00:00/prev_discharge">
previous discharge cath </a> results indicated no evidence of any significant occlusions.<br>
<br>
The
<a href="http://hww.st_mary.springfield/lab_CK_enz/987654321/14_May_1996/00:00/admit">
admission CK enzyme </a>results are above normal limits.<br>

</body>
</html>
```

Figure 18

Text As Viewed via Word Processor 14 or Browser

ID: 987654321
Date: 14-May-1996
Report type: Admission report
Written by: Dr. S. E. Markelson The admission ecg has clear evidence of left ventricular hypertrophy when compared to the current ecg for this patient.

The previous discharge cath results indicated no evidence of any significant lesions.

The admission CK enzyme results are above normal limits.

Figure 19

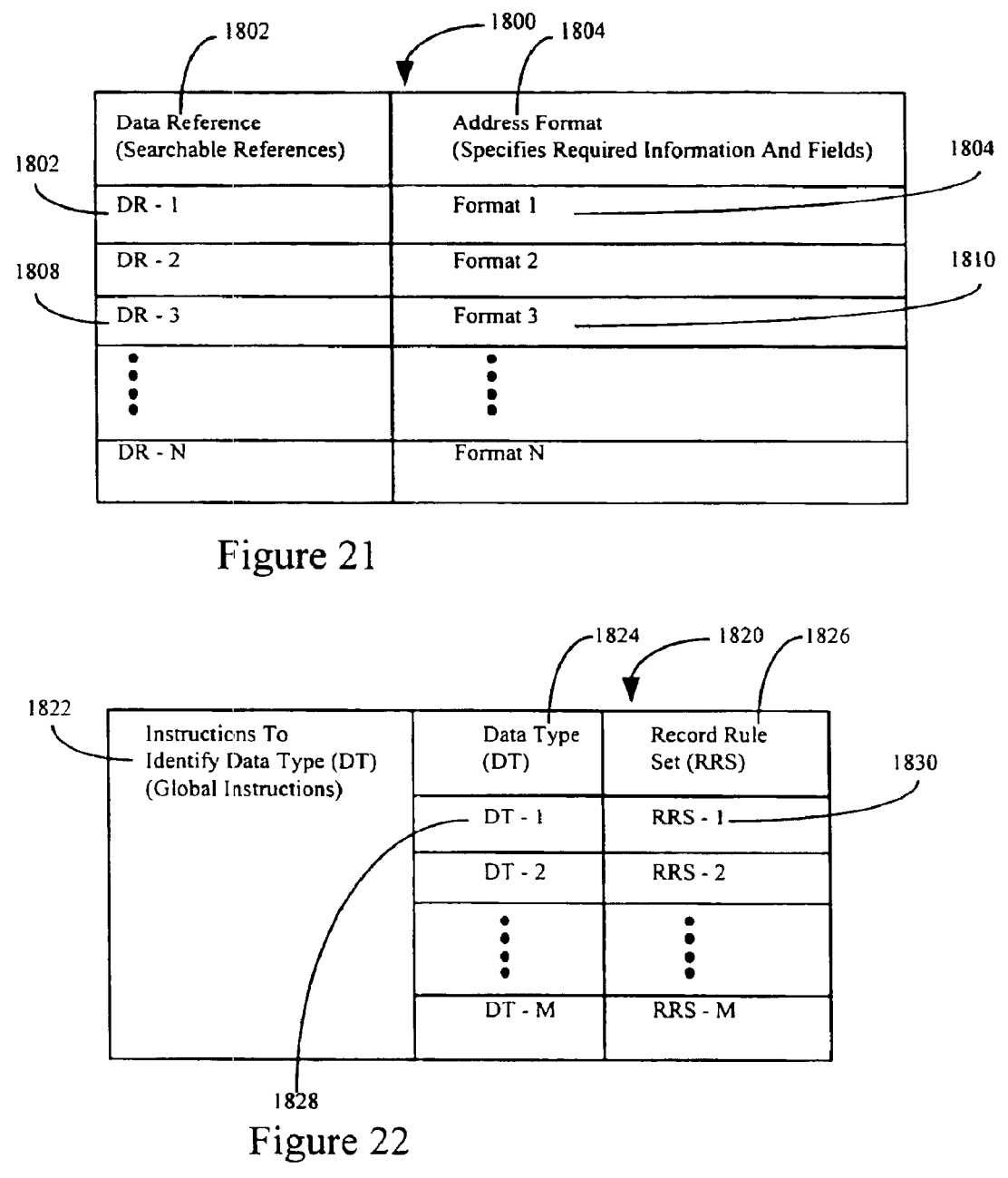

| | 1802 | 1800 1804 | |
|---|---|---|---|
| 1802 | Data Reference (Searchable References) | Address Format (Specifies Required Information And Fields) | 1804 |
| | DR - 1 | Format 1 | |
| 1808 | DR - 2 | Format 2 | 1810 |
| | DR - 3 | Format 3 | |
| | ⋮ | ⋮ | |
| | DR - N | Format N | |

Figure 21

| 1822 | | 1824 | 1820 1826 | |
|---|---|---|---|---|
| | Instructions To Identify Data Type (DT) (Global Instructions) | Data Type (DT) | Record Rule Set (RRS) | 1830 |
| | | DT - 1 | RRS - 1 | |
| | | DT - 2 | RRS - 2 | |
| | | ⋮ | ⋮ | |
| | | DT - M | RRS - M | |

| Data Reference (Searchable References) | Address Format | Record Rule Set (RRS) |
|---|---|---|
| DR - 1 | Format 1 | RRS - 1 |
| DR - 2 | Format 2 | RRS - 2 |
| DR - 3 | Format 3 | RRS - 3 |
| ⋮ | ⋮ | |
| DR - N | Format N | RRS - N |

Figure 23

METHOD AND SYSTEM FOR AUTOMATED DATA STORAGE AND RETRIEVAL

CROSS-REFERENCE TO RELATED APPLICATIONS

This patent application is a continuation in part of U.S. patent application Ser. No. 08/727,293 now U.S. Pat. No. 5,895,461 which was filed on Oct. 9, 1996 and is entitled "Method and System for Automated Data Storage and Retrieval with Uniform Addressing Scheme" which claimed priority from provisional application Ser. No. 60/023,126 which was filed on Jul. 30, 1996 and is also a continuation in part of U.S. patent application Ser. No. 08/871,818 now U.S. Pat. No. 5,903,889 which was filed on Jun. 9, 1997 and is entitled "System and Method for Translating, Collecting and Archiving Patient Records".

STATEMENT REGARDING FEDERALLY SPONSORED RESEARCH OR DEVELOPMENT

Not applicable.

BACKGROUND OF THE INVENTION

The present invention relates to the collection, storage, and retrieval of data on computer systems. More particularly, the present invention relates to a computer system for retrieving, modifying, and storing a plurality of topically, textually, or audio-visually related data records of a plurality of formats on a plurality of databases in conformance with a hypertext-linked, predefined topical organization.

When a patient is in a hospital, either as an inpatient or an outpatient, a variety of information concerning the patient may be collected and recorded. This may be in the form of observations, measurements, lab results, vital sign indicators, procedure reports and associated graphics. Over a long period of treatment, hundreds of pages of information may accumulate in the patient's record.

While the patient is in the hospital, it is typical that many different care givers, administrators, or insurance company employees will desire to view a part of the patient's cumulative record. The conventional paper chart is not always useful, as there is only one copy of it, and some laboratory tests may not be entered into the chart on a timely basis. To solve this problem, hospitals have used a variety of database systems such as hospital information systems (HIS) and clinical information systems (CIS) to store and present patient information on computer displays. However, there is still a substantial amount of data that does not get placed into these systems. A variety of factors may inhibit an automated process of comprehensive retrieval of a patient's data, such as incompatible communication protocols and formatting schemes between computer systems, non-digitized data records including pictures and standardized forms, and the lack of adequate computer interfacing support for low-cost medical instruments or devices. It is also typical that word processing documents, rather than being automatically collected by a database system, are simply printed in the form of a paper copy to be inserted into the conventional chart.

While various standardization committees have been established, e.g., HL-7, DOCOM, and IEEE, to develop common addressing schemes for hospital data, to date none have defined a consistent format to use for storing and retrieving data. For the sake of simplicity or due to limited resources, many manufacturers that use one or more of these standards choose to use only a portion of them; consequently their systems remain only partially compatible.

Furthermore, even many hospitals with database systems lack a centralized retrieval system because related hospital reports are often stored on separate databases. For example, a patient's radiology catheterization report and hemodynamic catheterization reports may be created and stored in separate databases, though as far as the physician who performed the catheterization procedure is concerned, these two reports are really just one procedure and should be associated with each other. For further example, a physician reviewing an admission report may find that it references laboratory tests or observations made contemporaneous with or previous to the patient arriving at the hospital. Should the physician decide to review these other records, she will have to perform additional searches to locate them. In some cases, this often cumbersome and time-consuming process results in care givers refraining from making complete use of the available patient information.

In many hospitals when a patient is discharged, a paper copy of these records is made and sent to the admitting physician for his own record keeping purposes. The collection, copying, and storage of all of these records is a very timeconsuming and labor-intensive activity. Further, the generally high risk of human error may manifest itself in the failure to return records to the correct patient's file or incorrect storage of a patient's entire file, effectively forfeiting the misplaced information. The physician is simultaneously confronted with the responsibility of filing and storing the paper copy in his own office.

Some hospitals have purchased laboratory or information systems capable of long term storage of various records. While this may assist the hospital in retrieving past records, it may not help the admitting physician in referring to them, for he may not have access to the data directly or may not have the specific software required to retrieve the data. So with such advanced systems the physician is still provided with a paper copy for his records.

Furthermore, many existing laboratory and information systems record information in a variety of inconsistent formats. Some of these formats are proprietary to the manufacturer of the specific system. Each system may use a separate database scheme to gain access to the data. Substantial efforts to get these systems to communicate with each other have not yielded satisfactory results. For example, many large medical information systems use complicated data exchange protocols; but these protocols are unwieldy for simple, often portable instruments which lack the hardware and software capacity to conform to such protocols.

Some reports may be created using a wordprocessor. These may originate in a department of the hospital or in a physician's office. These reports, which may be kept in a conventional file cabinet, are not always included with the rest of the patient's reports.

What is needed is an effective alternative to creating paper records that must be copied and meticulously tracked, an alternative that would permit physicians to access the data economically and easily in their own offices. Such a system would permit a system user to enter a keyword to retrieve a specific data record of a patient, retrieve the requested record from whichever database it is stored to, reformat the data record with hypertext links to related patient records, and return the requested record to the system user for display on a browser. The system would preferably use a mark-up language such as the well-known Hypertext Markup Language (HTML) or JAVA so that it could utilize inexpensive, standard software packages. The system would also be operable to format data records stored on the various databases of the computer network systematically, periodically, or automatically upon the creation of new, or the modification of existing, data records. The system would be operable to collect all data records pertaining to a specific patient, doctor, or other subject, modify them to support display through a Java applet, internet browser, or other universal display standard, generate additional patient files to organize the data records in a hypertext directory structure, and store the data records and files on a mass-media storage device such as a CD-ROM.

In addition, it would be advantageous to have a system which permits both the storage and the retrieval of data records according to a standardized addressing scheme which can be determined solely by the use of certain keywords known to the various users of the system. Such a system could employ standard word processing software to enable multiple users to create and reference the various data records. The system would recognize certain keywords entered by the user during creation of the data record and use those keywords to determine the appropriate location (e.g.; database, directory and file name) to store the record according to a predetermined addressing scheme. Similarly, it is desirable for the users of the system to be able to locate particular data records using a few keywords without having to know the complexities of which database the record is on, the format of the record, the file name or the directory address.

BRIEF SUMMARY OF THE INVENTION

It is an object of this invention to provide a means of processing and converting existing data records formatted, structured, and accessed according to a multitude of disparate standards to common standards by which they may be accessed, controlled, and/or displayed through a single interactive display program. It is another object of this invention to provide conventions for exploring data records for references to contextually related data records and modifying, generating, embedding, and appending links and data-retrieving codes in and to said related data records, whereby to organize said related data records in a hypertext tree structure. A further object of this invention is to store a group of related data records organized in a hypertext tree structure to a mass storage device, such as a hard disk or CD-ROM, through which the data records may be retrieved, displayed, and controlled through a single interactive display program. In order to minimize costs and maximize end-user accessibility, the standards and conventions used by the present invention for modifying data records and addressing schemes facilitate display through a widely-familiar and low-cost display program such as an Internet browser.

The invention may be adapted for use in a wide variety of applications, and is suitable for any environment in which numerous data records having one or multiple forms and/or formats are to be collected, stored, archived, retrieved, or translated. By way of illustration and not by way of limitation, the invention is presented in the context of a hospital environment, in which typically there are numerous computer systems in use by various health care professionals in one or several hospitals, and each professional often desires to have access to the patient records created by other professionals in that or other hospitals.

A typical setting for the present invention provides multiple databases and workstations linked via a network wherein the databases store data records in a variety of formats and the workstations utilize user interfaces to input, retrieve, and manipulate data records. The present invention utilizes specification tables identifying each of the information processors or databases used by the hospital, the types of data records stored by the databases, and instructions and algorithms for accessing, modifying, and processing data records and their addresses, depending on the data type. Similar specification tables are also kept to identify each workstation where wordprocessor, spreadsheet, or other records, including those downloaded from portable medical devices, may be held.

When a system user at a workstation linked to the hospital computer network equipped with the present invention submits a request for a particular patient record, the invention parses the data request for an address root and other pertinent information about the data record to be retrieved, which may include the time and date the data record was created or last modified and a patient ID. Using this information incorporated in the data request and in the specification tables, the invention modifies the existing data request into a URL or other addressing convention, as necessary, to retrieve the data record from the appropriate database.

After retrieving the data record, the invention may modify it to make it compatible with a standard supported by the common interactive display browser used by the system. For example, the invention may convert a text document to an HTML document or convert graphics, video, or audio records to browser or Java-enabled formats. Further, depending on the formatting specifications for a particular data type, the invention may identify key words, links, and programming codes embedded in the data record, modifying them and inserting additional hypertext links and programming codes as necessary. For example, it may be desirable that a hypertext link referencing the patient's demographics and insurance information be inserted into each record reporting on the patient's condition, status, or profile for quick and easy referral. As another example, it may be desirable to place a hypertext link in a radiology catheterization report that references the hemodynamic catheterization report and vice versa so that each refers to the other.

In this manner a hospital may use Internet or Intranet compatible databases with databases that are not compatible, and may choose to use URL addresses of its own choice independent of what the individual vendors have chosen. The administrator may also preprogram the data translation and collection system to link reports together as appropriate, so that care givers may more quickly and directly refer to relevant or related information. The translation process described here may be used on a dedicated system for this purpose or may be distributed among several processors including those of the database systems.

Another aspect of the present invention includes means for receiving, processing, and storing hospital records systematically, periodically, or automatically as they are created or modified. In this mode of operation data records may be preformatted according to the hospital's specifications, allowing for quicker record retrieval during subsequent data requests. The translation operation may be allocated to a dedicated system for this purpose or may be distributed among several processors, including those of the database systems.

A further aspect of the present invention includes means for periodically retrieving and filing the contents of a designated area of each workstation's disk. For example, word processing documents generated at a workstation may be stored in a designated area, such as a special "collection" drive or folder, to which the hospital computer network has access. The invention would retrieve the data records stored in the collection folder, and identify, interpret, and modify them before storing them in an appropriate database.

Yet another aspect of the present invention includes means for retrieving, processing, and storing all of a patient's data records that are available on the hospital's computer network onto a mass media storage device, such as a CD-ROM. For example, this process may be initiated by submitting a collection request identifying the patient's ID number or other identifier uniquely identifying the patient. The invention submits requests, passwords, macros, and programming codes, as appropriate, to each of the databases and workstations that include portions of the patient's cumulative record. Each record retrieved is processed and modified as above—as if the particular record had been requested by a system user. The invention not only collects applicable data records, but also multimedia clips, applets, browser extensions, "plug-ins," and other application modules addressed by programming codes embedded in the patient's data records. Substitute files explaining the absence of a linked record or module are created for data records or modules regarded as inappropriate for storage and distribution on an unsecured or uncontrolled medium. The invention would also create a "master file for the patient analogous to a "home page" for a website or the root directory of a tree structure, containing links to other patient-related files and data records. The master file may have hypertext links to patient records and to additional (secondary) control files, which in turn have hyperlinks to more patient data. After completing these collection routines, the invention would transfer the collection of data records, applets, browser extensions, and other data and programming modules to a mass-storage device. In this manner a patient's cumulative patient record could be stored on a single CD-ROM or other high-density storage device, cheaply distributed to other hospitals or health care professionals serving the patient, and be conveniently accessed by those hospitals and health care professionals.

The present invention also provides a wordprocessor employing a standardized addressing scheme, wherein the wordprocessor recognizes keywords entered by a user who is either creating and storing a data record or attempting to locate a data record among numerous data records at different addresses on a plurality of computer databases.

Thus, the present invention provides first a plurality of databases on which a variety of data records are stored. The databases are in communication with one or more processors which interpret input data from a user interface and direct the storage and retrieval of data records. The databases and processors may be linked via a network, or one or more of the databases may communicate locally with an associated processor, as in a personal computer. The invention also provides a plurality of user interfaces, such as combinations of keyboards, video displays, microphones with voice recognition, and other input devices (e.g. rf receiver, etc.), through which system users create, store, retrieve and display data records. These user interfaces can be simple terminals which communicate with a processor and a database over the network, or they can be part of an integrated interface/processor combination, such as in a personal computer.

For accepting keywords from the user and determining the storage location of a data record to be stored or retrieved, the invention includes a wordprocessor having certain defined functions. For the creation of data records, the wordprocessor accepts various information from the user to identify the user and the: type of record being created, as well as other information which may uniquely identify the record and its storage location after the record is completed and saved, or "published." The wordprocessor uses these keywords, or specialized information fields, to determine the location at which the record is to be stored and employs a standardized addressing scheme compatible with or comparable to the Universal Resource Locator (URL) addressing used on the global computer network (Internet). The wordprocessor automatically creates a link between the keyword in the data record and the address of the data record on the computer system.

The wordprocessor also includes a function which compares text entered by the user to a predetermined list of keywords known to be used in the system and may prompt the user for a different keyword when no match is found. Once the user enters a sufficient number of recognized keywords to uniquely identify the data record being created or sought, the wordprocessor determines the unique address of the data record according to a predetermined, standardized addressing scheme so that the record may be stored or retrieved.

When a data record is created and stored, the wordprocessor creates a link, in the manner of a hypertext link, between a keyword uniquely identifying the particular record and its unique address (URL) on the computer system. To this end, the wordprocessor identifies background information within the record and uses the background information and, in some cases, the keyword itself, to form the address link pointing to the record. This link points to the unique address of the record and will enable other users to retrieve the record when the same keyword is used in a request for a data record. In the same manner, other data records containing this same keyword will contain a link to that record, permitting users to create data records which refer to other data records by use of a hypertext link.

The wordprocessor included in the invention contains a monitoring function which monitors free text entered by the user to determine whether the user is creating a hypertext reference at a place in the data record other than in a specified keyword field. This monitoring function continuously surveys text/data being input by the user so that hypertext links in a data record or report can be created by the user at will.

The wordprocessor also includes an editing function which permits keywords, or hypertext references, in data records to be edited and determines whether a user is changing the keyword to another keyword or a non-keyword. This editing function attempts to match changed keywords with other known keywords to determine whether the user is referencing a different data record. The wordprocessor treats keywords or keyword phrases as singularities which cannot be edited without either deleting the link (URL or hyperlink) associated with the keyword or changing the hypertext link to a different hypertext link.

The addressing scheme and hypertext links of the invention are suitable to be created by and used with conventional tools in common use for publishing documents on the Internet. Data records containing keywords and hypertext links may be created in a markup language such as Hypertext Markup Language (HTML), and the addressing scheme may comport with Internet URL addressing. Thus, the invention provides internet/intranet capabilities and may be operated with relatively inexpensive, commercially available HTML formatting software and Internet browser software. Other hypertext link preparation methods and other addressing schemes are possible.

The invention further includes a system for linking first record references to a first record wherein the references are in a second record, the system comprising a database (DB) including at least one address format specifying an address format of the first record address and a processor linked to the DB and running a pulse sequencing program to perform the steps of receiving the second record, analyzing the second record to identify references to the first record and when a first record reference is identified, using information from the second record to form the address of the first record as specified by the address format.

Preferably the address format also specifies required information for forming the address for the first record, the DB further includes at least one record rule set (RRS) corresponding to the address format, the RRS specifying rules for gleaning the required information from a record and, wherein, when the first record is referenced in the second record, the processor gleans the required information from the second record in the manner specified by the RRS.

Also, preferably, the DB also includes a data reference (DR) which is associated with the address format and wherein, when searching for a reference to the first record, the processor searches for instances of the DR. In one aspect the program includes a wordprocessor, the DR is a text name associated with the first record and the first record address is a markup language data reference.

In one embodiment the system is also for creating markup language data references between the first record references and the first record, the processor also, when a first record reference is identified, provides the first record reference to a user as a selectable segment and links the selectable segment to the first record via the first record address such that, when the selectable segment is selected, the first record is provided to the user.

Where a selectable segment is provided, the processor may further, after the selectable segment is provided, perform the steps of, when the second record is accessed, monitor changes to the second record and, when the selectable segment is modified, de-linking the selectable segment and the first record.

In another aspect the DB includes a plurality of address formats and their associated RRSs and DRs. In this case, the processor searches the second record for any of the DRs and, when any of the DRs is identified, the processor identifies the associated address format and RRS, gleans the required information from the second record in the manner specified by the associated RRS and forms the address corresponding to the first record.

In yet another aspect the system includes an interface for entering the second record, the second record entered in record segments and, wherein, the processor runs the program as second record segments are entered via the interface.

In another aspect the system is for use with a data specifying device wherein the step of receiving includes receiving the second record from the data specifying device.

Furthermore, the invention includes a system which receives database records, each record including a separate information set and characterized by at least one data type, for a specific record, the system using the specific record's information set to construct a record address which enables easy subsequent record access, the system comprising a database (DB) including at least one address format which is associated with the at least one record type and which specifies a unique set of required information to form a record address for the record type. The system also including a processor linked to the DB and running a pulse sequencing program to perform the steps of, for the specific record receiving the information set, confirming the data type and the associated address format, analyzing the information set to glean the required information, using the required information to form a record address as specified by the address format and storing the record at the record address.

In one embodiment there are a plurality of data types, the DB includes a separate address format for each of the different data types and the step of confirming includes the steps of determining the data type and the associated address format.

In one embodiment the DB further includes at least a separate record rule set (RRS) corresponding to each of the address formats, each RRS specifying a unique set of rules for gleaning required information from a record and, wherein, the processor gleans required information in the manner specified by the RRS.

Preferably the program is a first application program and the processor also performs a second application program to link stored records which are referenced in a first record to the referenced records, to this end the processor further performing the steps of, after at least one record is stored, searching the first record for a reference to a stored record, when a reference to a stored record is identified, determining the address associated with the referenced record, providing the reference to a user as a selectable segment and linking the selectable segment to the referenced stored record via the record address such that, when the selectable segment is selected, the record is provided to the user.

Preferably, the processor provides a data reference (DR) for the record information set, the DR useable to refer to the record in other records, the processor, when searching for a reference in the first record, searching for the DR.

Also, preferably, after the record address is formed, the processor also correlates the DR with the record address and stores the DR along with the record address, the processor determining the address associated with a reference by identifying the address associated with an identified DR.

In one embodiment the RRS is a first RRS and the DB also associates a second RRS with the address format, the second RRS specifying rules for gleaning the required information from the first record, when a DR is gleaned from an information set, the processor also correlating the DR with the address format and storing the DR along with the address format, the processor determining the address associated with a reference by, when a DR is identified, identifying the address format associated with the DR, identifying the second RRS associated with the identified address format and the required information specified by the identified address format, gleaning the required information from the first record as specified by the second RRS and forming the record address using the required information and as specified by the address format.

The invention further includes a system which receives database records, each record including a separate information set and characterized by at least one data type, for a specific record, the system using the specific record's information set to identify a record address which enables easy subsequent record access. The system is also for use with a data specifying device which provides the database records, including at least one field specifying a data reference. The system comprises a receiver for receiving records from the specifying device and a processor linked to the receiver and running a pulse sequencing program to perform the steps of, for a specific record, receiving the information set, identifying the DR, using the DR to identify a record address for the record and storing the record at the record address.

The specifying device may be a hand held device or a database or some other suitable specifying device (e.g. a dictaphone). In addition, the specifying device, in addition to specifying the DR, may also specify other information which is used to identify the address.

According to yet another embodiment of the invention, a record being searched may be characterized by a data type and the data type may be associated with a specific RRS for gleaning information therefrom and, when a DR is identified in a record, the system may determine the data type of the searched record to identify the RRS to be used to glean the required information.

Moreover, the invention further includes methods to be used in conjunction with the systems described above.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIGS. 3A and 3B are tables showing the contents of the "Database Table" and "File Format Instruction Table" maintained and used by the data translation and collection system to access, translate, reformat, and store data records kept on databases on the medical computer network;

FIGS. 4A and 4B are tables showing the contents of "List of Workstations" and "Report List" maintained and used by the data translation and collection system to access, translate, reformat, and store data records kept on workstations on the medical computer network;

FIG. 6A is a graphical representation of a master file in HTML format through which all of a single patient's medical records created at a hospital equipped with the present invention may be viewed;

FIG. 6B is a graphical representation of the master file of FIG. 6A as viewed by a system user with a network browser;

FIG. 7A is a graphical representation of a secondary control file in HTML format providing a hypertext-link embedded discharge report;

FIG. 7B is a graphical representation of the secondary control file of FIG. 7A as viewed by a system user with a network browser;

FIG. 8A is a graphical representation of another secondary control file in HTML format providing a structured list of hypertext links to a plurality of cardiology reports;

FIG. 8B is a graphical representation of the secondary control file of FIG. 8A as viewed by a system user with a network browser;

FIG. 9A is a graphical representation of a tertiary control file in HTML format providing a list of electrocardiogram reports;

FIG. 9B is a graphical representation of the tertiary control file of FIG. 9A as viewed by a system user with a network browser;

FIG. 14D is a textual representation of the report of FIG. 14C as modified to include data references in the form of HTML codes;

FIG. 17 is a is a graphical representation of a sample patient report during its creation by a user of the computer system according to the invention;

FIG. 18 is a graphical representation of text of the report of FIG. 17 after being converted to HTML format and having hypertext links to URL addresses substituted for their associated data references;

FIG. 19 is a graphical representation of the report of FIG. 17 with hypertext links, as viewed by a system user with a network browser or other request handler routine;

FIG. 21 is a table used by the wordprocessor of the present invention to build data base addresses for linking first record references in a second record to the first record;

FIG. 22 is a table used in conjunction with the table of FIG. 21 for gleaning information from a second record which is required to form a data base address for a first record which is referenced in a second record; and FIG. 23 is a table similar to the tables of FIGS. 21 and 22 which is used in another embodiment of the present invention to build data base addresses for linking first record references in a second record to the first record.

DETAILED DESCRIPTION OF THE INVENTION

Figure 1:
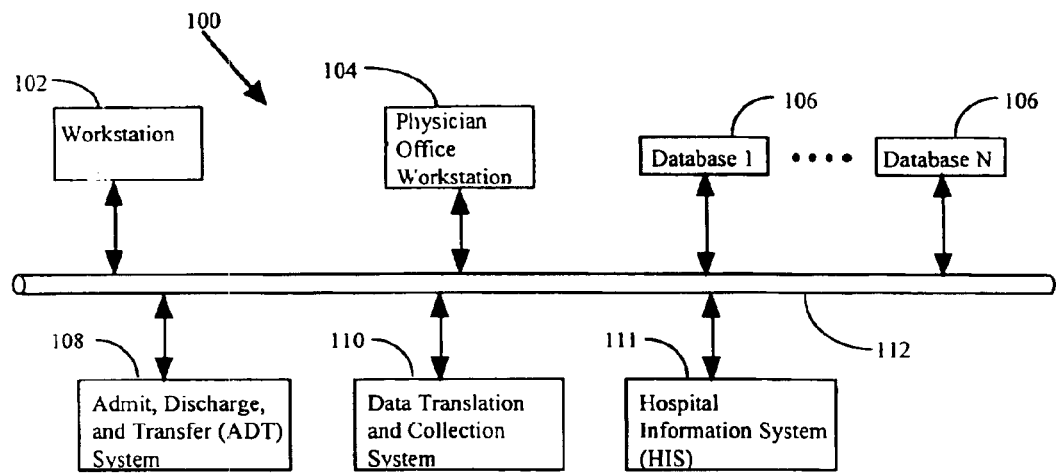
FIG. 1 is a block diagram of a medical computer network according to the present invention, including a plurality of databases for data record storage and a data translation and collection system.

Referring now to FIG. 1, the invention is illustrated as a medical computer network 100, including a plurality of hospital based workstations 102 (which may be personal computers), a plurality of physician office workstations 104 which may also be personal computers, a plurality of databases 106 which may be provided by a multitude of vendors with separate data structures and data elements. The computer network 100 may also comprise an Admit, Discharge, and Transfer (ADT) system 108, a data translation and collection system 110, and a Hospital Information System (HIS) 111. The data translation and collection system 110 is not necessarily a separate physical element of the medical computer network 100, but is represented that way in the preferred embodiment for purposes of illustration only. It may be alternately recognized as a program application or even an aspect of a network operating system, the operations of which may be distributed over and performed by many different processors, workstations, and databases on the medical computer network 100.

Databases 106, computer systems 108, 110, 111, workstations 102, and physician office workstations 104 may communicate with each other via a communication network 112, which may be a combination of local and wide area networks, using Ethernet, serial line, wireless, or other communication standards. Communication network 112 may also be arranged in such a manner to be part of the Internet or as an individual Intranet. Each workstation 102, 104 includes a "collection" folder 105, a user interface 103 which may include a network browser or similar display, entry, and retrieval program, a separate database 2 and a special wordprocessor 14. User interface 103 may be any means for permitting users to create data records and/or retrieve data records from the medical computer network 100 capable of supporting a network browser, such as well known keyboard and video terminal combinations or voice recognition hardware and software.

Wordprocessor 14 runs under the direction of user interface/processor 103 and governs the creation of data records, the recognition of keywords in the data records, the composition of hypertext links between the keywords and the data records, and the retrieval of data records in response to keywords input to the wordprocessor by the user or contained within a data record.

Figure 2:
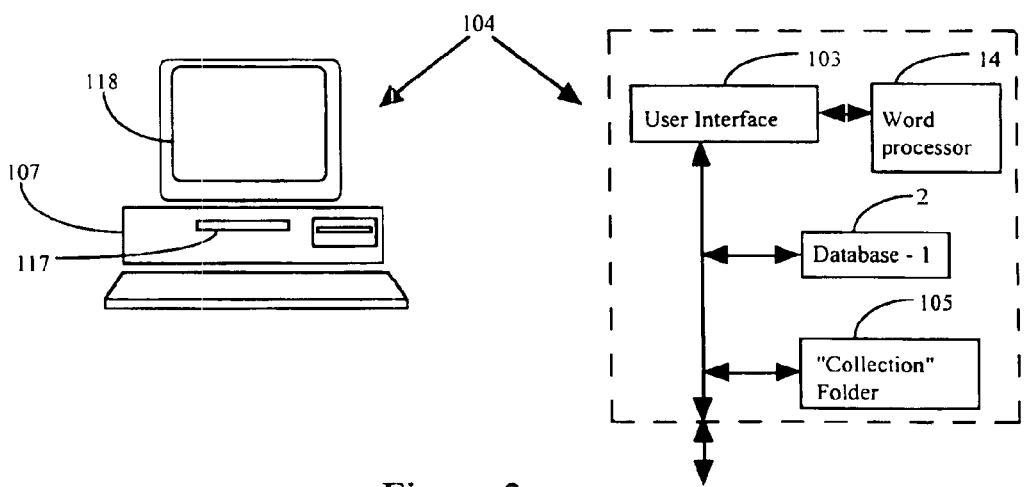
FIG. 2 is a graphical illustration of a physician office workstation.

FIG. 2 shows a typical physician office workstation 104 comprising a personal computer 107 which may include a display 118, and a CD-ROM drive 117 or other means of mass storage which may be removable.

The data translation and collection system 110 maintains a file referred to as Database Table 130, whose contents are partially seen in FIG. 3A. For each database 106 included on the medical computer network 100, an entry is made in the Database Register 131 of the Database Table 130. Corresponding to each entry in the Database Register 131 is an address or addresses field 132 used to access the database on communication network 112 and a separate File Format Instruction Table 134.

A partial list of the contents of File Format Instruction Table 134 is seen in FIG. 3B, which includes records of each data type 136 stored by the database 106. Corresponding to each data type 136 in File Format Instruction Table 134 is a set of special instructions or program codes 142 used to translate a request for such data to a format appropriate to the data type and database from which the requested information may be retrieved. Also corresponding to each data type 136 is a hypertext cipher or record rule set (RRS) 138 providing special instructions or codes used to add data references (such as hypertext links) and to format the data, which instructions or codes may include decompression algorithms. In addition, the RRS 138 also specifies rules for gleaning information from a record which can be used to form a record address. Hereinafter the terms hypertext cipher and RRS may be used interchangeably to mean the same thing.

Further corresponding to each data type 136 is a URL cipher or address format 140 used to generate an address to store the designated type of data. The address format 140 specifies information which is required to form an address for an associated record type and also specifies the order of the information in the resulting address. Hereinafter the terms address format and URL cipher may be used interchangeably to mean the same thing.

Figure 10:
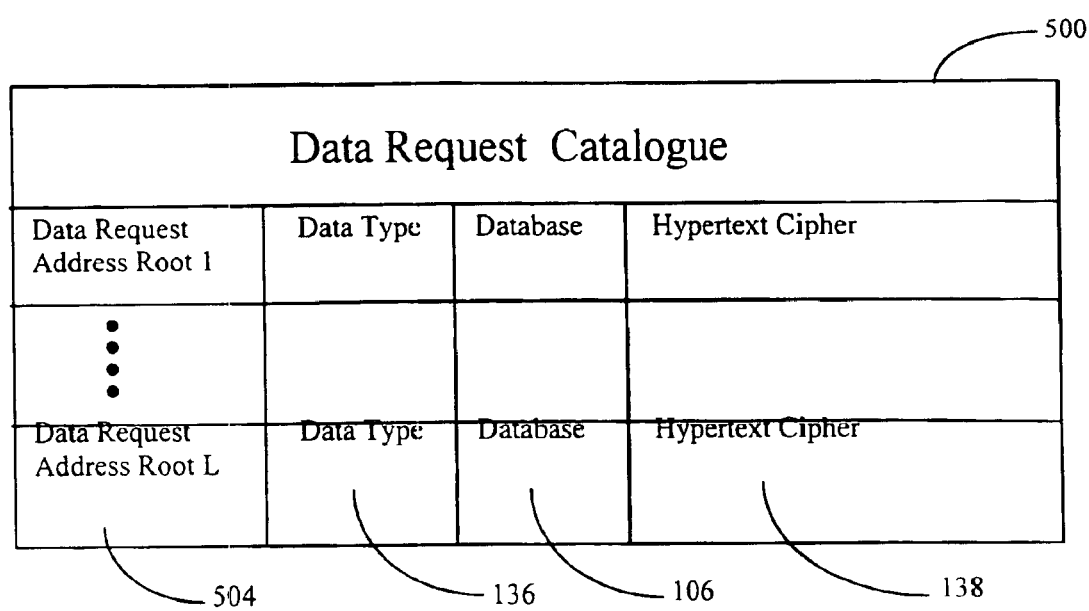
FIG. 10 is a table showing the contents of the "Data Request Catalogue" maintained and used by the data translation and collection system to discriminate the data type and database location of a requested data record from the alphanumeric string requesting the data.

The data translation and collection system 110 may also retain a file referred to as Data Request Catalogue or database table (DBT) 500, whose contents are partially seen in FIG. 10. The Data Request Catalogue or DBT 500 includes an array of Data Request Address Roots or data references (DRs) 504, to each element of which corresponds fields identifying the data type 136, the database 106 in which the data type is located, and hypertext cipher 138 (which is kept also in the File Format Instruction Tables 134 (FIG. 3B) of the Database Table 130 (FIG. 3A)). This file may be accessed when a request for data is received by the data translation and collection system 110 to recognize the matching data request address root 504 which identifies the data type 136 and the database 106 on which it is kept.

A. Responding to Data Requests and Providing Translation

Figure 12A:
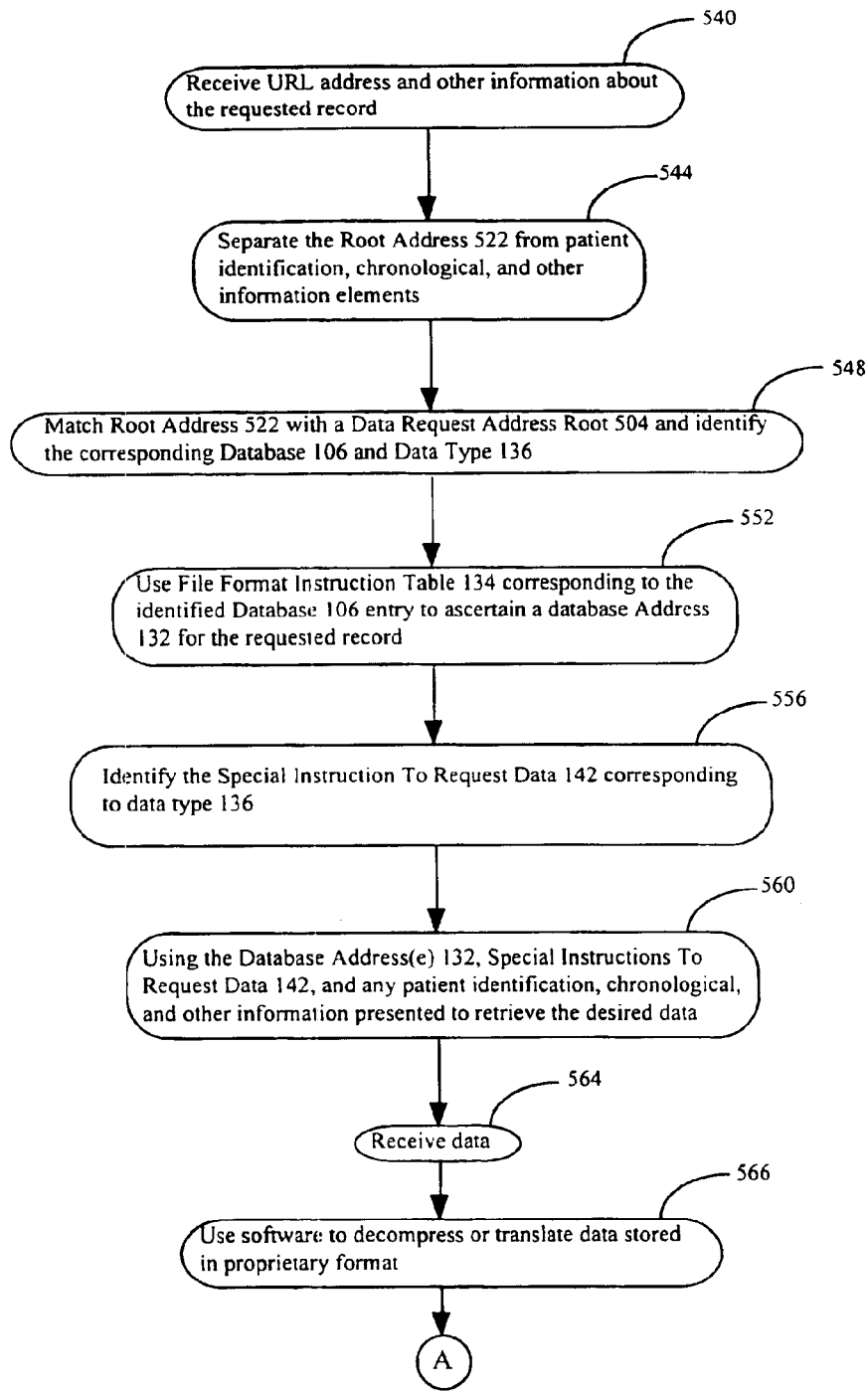
FIGS. 12A–12C are a functional flow chart showing the steps used to receive a request for a data record, translate the request, retrieve the data record, and reformat the data record prior to sending it to its requested destination.
Figure 12B:
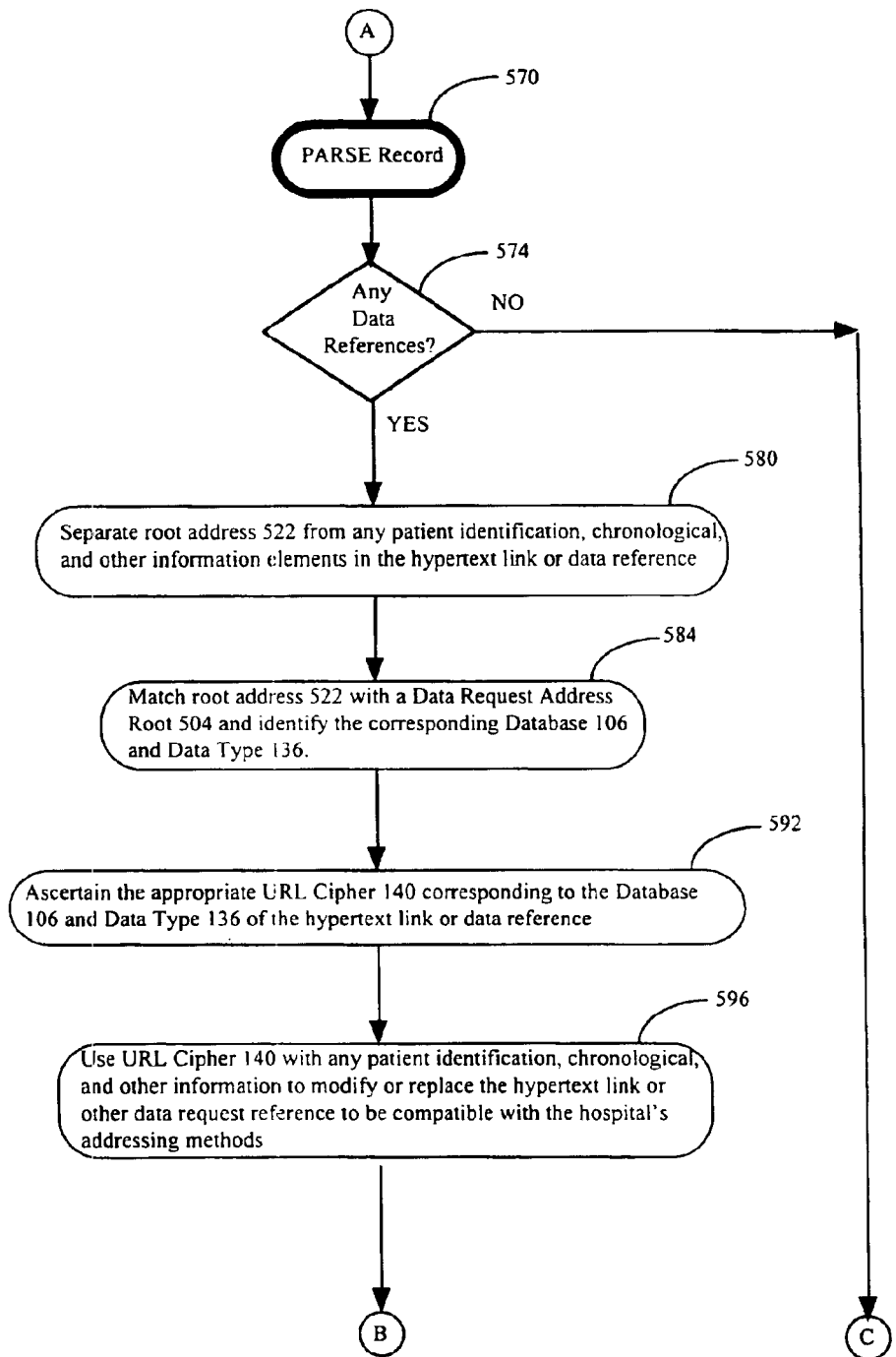
Figure 12C:
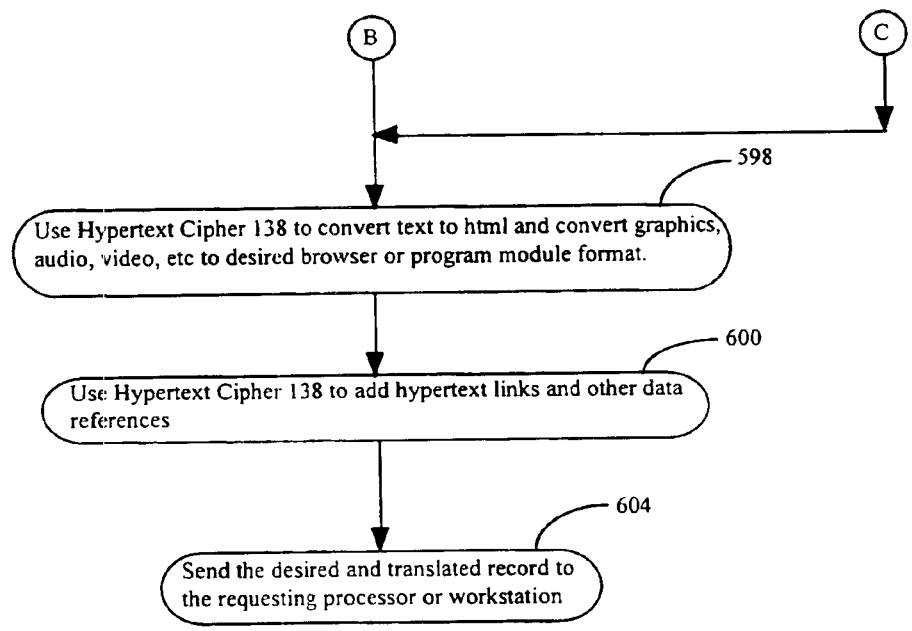

FIGS. 12A–12C describe the operation of the data translation and collection system 110 (FIG. 1) in responding to requests to retrieve data, translating those requests to conform to the format required by the applicable database, retrieving the data, reformatting the data, and delivering the data to the appropriate destination.

Figure 11:
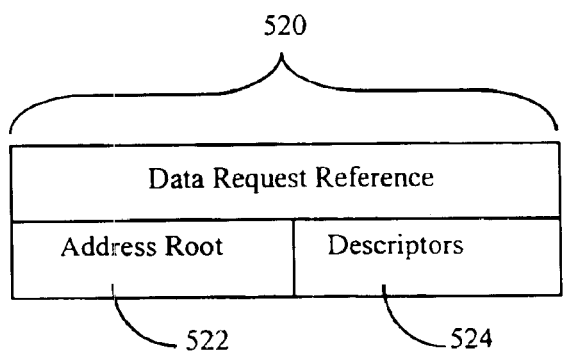
FIG. 11 is a graphical representation of a data request containing an address root and descriptor.

Commencing with FIG. 12A, in step 540 the data translation and collection system 110 receives a data record reference 520 (FIG. 11) in the form of a data request containing an address root 522 and descriptors 524 about the requested record. In some instances, a data request will originate from a system user accessing a hypertext link on a document displayed by the system's interactive display browser. In other instances, the data request will originate from a database or workstation application program. There may be several non-uniform but mutually distinguishable data request formats among the several hospital databases 106 (FIG. 1) on the medical computer network 100 (FIG. 1). Alternately, data requests may be uniformly and compatibly formatted for all records stored by various hospital databases 106 (FIG. 1). For example, the data requests may be in the form of a URL with optional data fields sent with it to assist in identifying the record to be retrieved.

In step 544, the address root 522 (FIG. 11) of the data record reference 520 may be determined by removing the descriptors 524—any patient identification, chronological details, or other non-addressing information—from the received data request. The descriptors 524 are temporarily stored for use in step 560.

In step 548, a search is performed to locate a match for the address root 522 (FIG. 11) of the data record reference 520 among the data request address roots 504 (FIG. 10) listed in the data request catalogue 500 (FIG. 10). By finding a matching data request root address 504, the invention immediately identifies the data type 136 (FIG. 10), the database 106 used to store this data, and the hypertext cipher 138 providing special instructions used to format and add data references to the data.

In step 552 the database 106 identified in step 548 is in turn referenced in Database Table 130 (FIG. 3A) to its corresponding File Format Instruction Table 134 (FIG. 3A) to determine the address(es) 132 (FIG. 3A) of the database 106 storing the data.

In step 556 the data type 136 identified in step 548 is cross-referenced with the File Format Instruction Table 134 (FIG. 3A) identified in step 552 to locate the special instructions to request data 142 (FIG. 3B) used to translate the request to a format appropriate to the data type and database from which the requested information may be retrieved. These instructions may, for example, include passwords or macros needed to retrieve the data.

In step 560 a code is constructed using the database address(es) 132 identified in step 552, the special instructions to request data 142 identified in step 556, and the descriptors 524—the patient identification, chronological details, or other non-addressing information-stored in step 540. The code is submitted to the appropriate database to produce the requested data record.

After the database has produced the requested data record, the record may in step 564 be received by the data translation and collection system 110 for additional processing.

The steps by which the data translation and collection system 110 processes the selected data record are shown in FIGS. 12B and 12C. In step 566, the system uses the hypertext cipher 138 to determine whether or not the data is stored in a proprietary format. If it is, the applicable proprietary software is used to decompress or translate the data. This may be done on the manufacturer's database 106, another computer processing system, or by the data translation and collection system 110 itself.

In step 570, the record is parsed, discussed infra, to locate date references: hypertext links, multi-media requests, and key words or phrases. If none are found, the process advances to step 598, discussed infra.

If there are data references, they may in steps 580 through 596 be reformatted so that the URL addresses are compatible with addressing protocols used by the hospital. In step 580, the address root 522 (FIG. 11) of the hypertext link or other data record reference 520 may be determined by removing the descriptors 524—any patient identification, chronological details, or other non-addressing information-from the received data request. The descriptors 524 are temporarily stored for use in step 596. In step 584, a match for address root 522 is sought among the data request address roots 504 (FIG. 10) listed in Data Request Catalogue 500, which locates the Database 106 and Data Type 136 corresponding to the matching Data Request Address Root 504. In step 592, the identified Database 106 and Data Type 136 are referenced in Database Table 130 (FIG. 3A) and the corresponding File Format Instruction Table 134 (FIG. 3B) to acquire the appropriate URL cipher 140 (FIG. 3B). In step 596, the URL cipher 140 processes the descriptors 524—the patient identification, chronological detail, and other information—extracted in step 580 to modify or replace the hypertext link or other data reference found in the selected record. Steps 580 through 596 may be performed for each hypertext link and reference to other data records found in the selected record.

For some types of data records, the URL cipher 140 will generate addresses compatible with database formatting standards such as SQL or Oracle.

In step 598 the data translation and collection system 110, using the Hypertext Cipher 138, converts any text portion of the selected data record into a browser compatible format, such as HTML format, and any graphics, audio, video, or other non-text information into a browser, plug-in, or Java compatible format.

In step 600, the data translation and collection system 110 inserts hypertext links or other references to the selected record in accordance with the hypertext cipher 138 identified in step 548. If directed by the hypertext cipher 138, the record may also be interpreted and modified or reformatted.

In step 604, the data translation and collection system 110, having retrieved and translated the requested record, forwards the record to the destination selected by the requesting workstation or processor.

B. Receiving Patient Records for Translation and Address Formatting

Figure 13A:
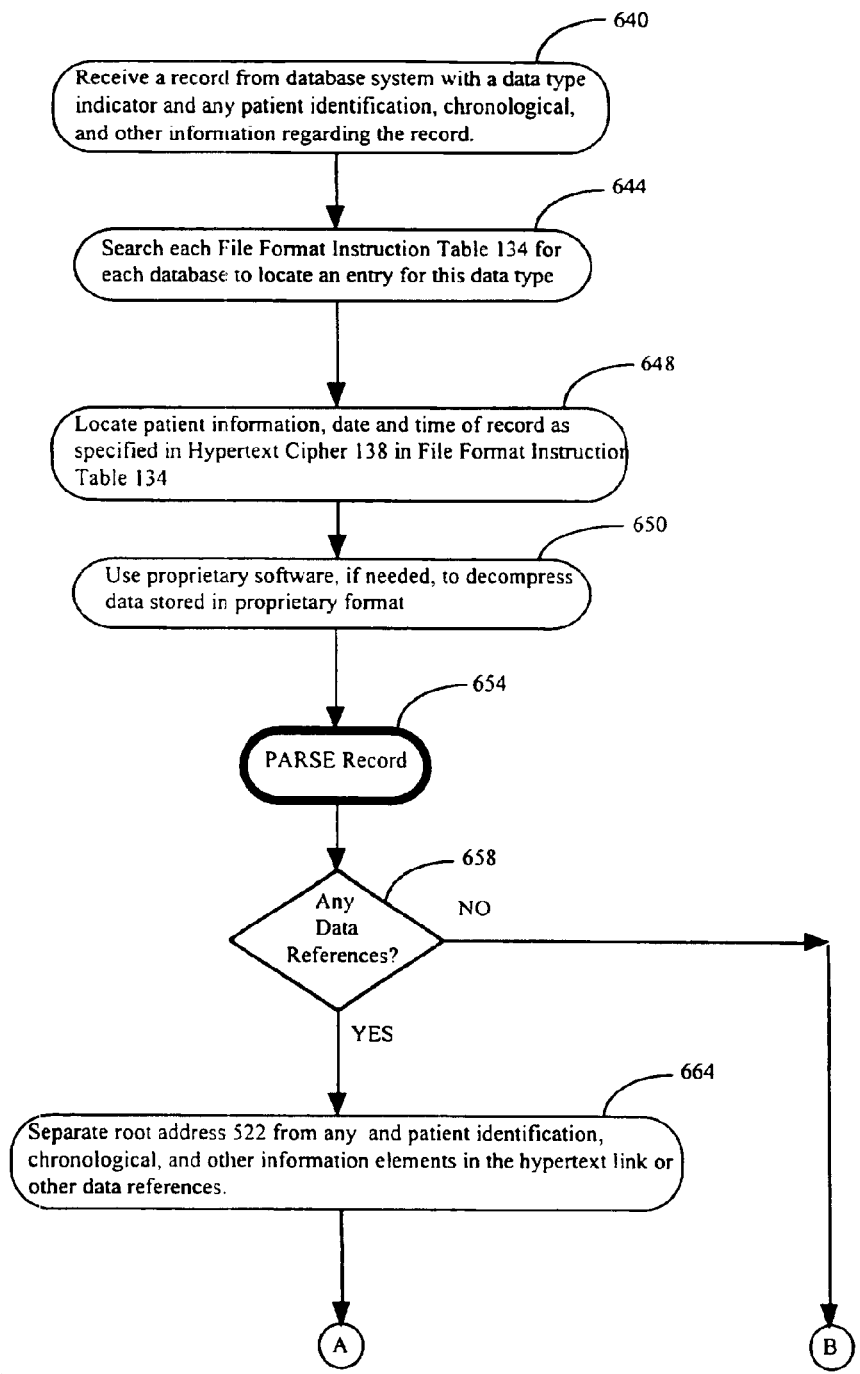
FIGS. 13A–13C are a functional flow chart showing the steps by which the data translation and collection system processes a data record received or retrieved from a workstation or database system on the medical computer network, reformat the data record, assign it a URL address, and deliver it to a database for storage.
Figure 13B:
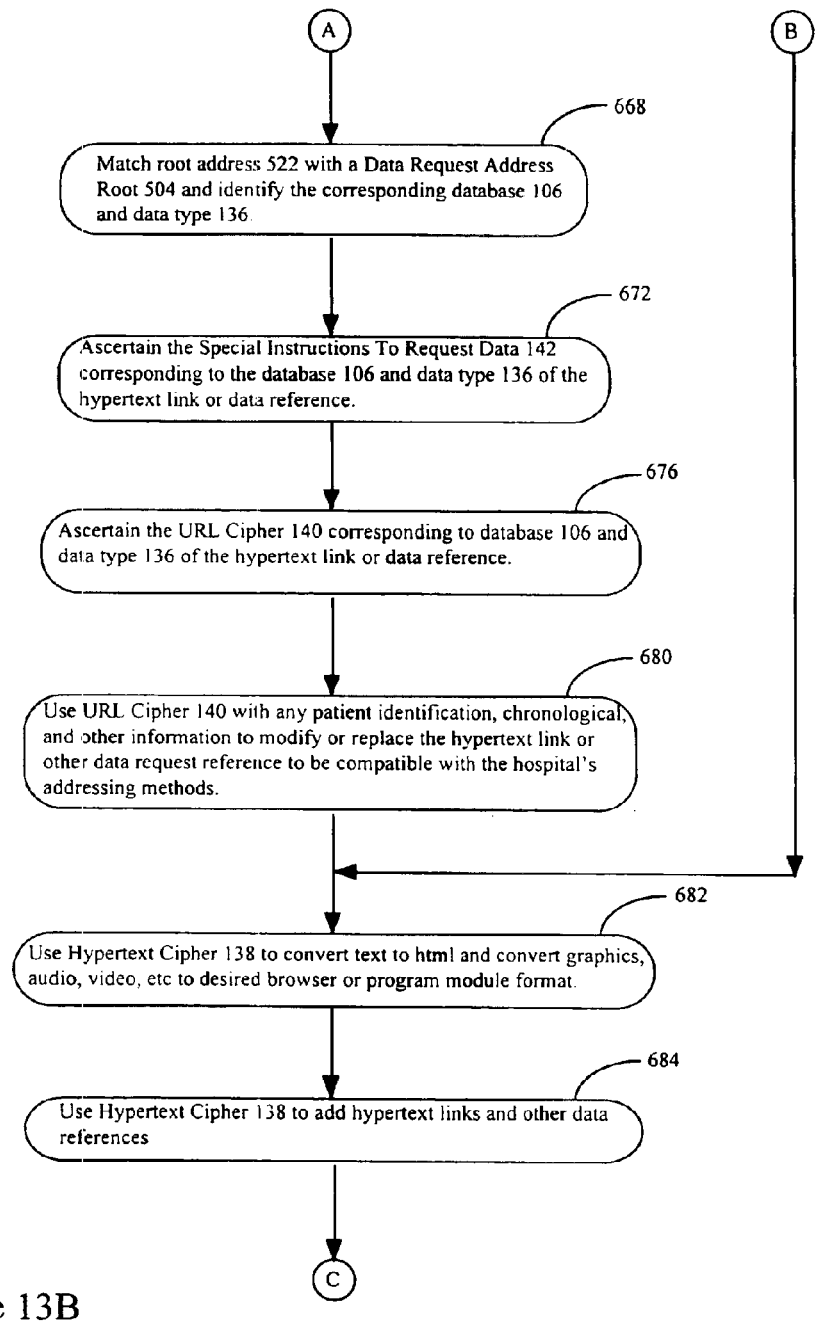
Figure 13C:
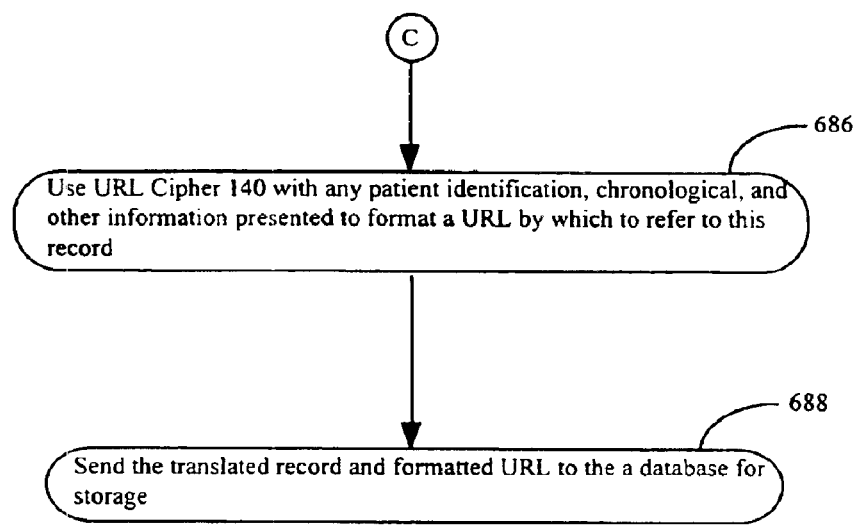

FIGS. 13A–13C set forth an alternate embodiment of the operation of the data translation and collection system 110 (FIG. 1) with particular reference to receiving, translating, and formatting data records to facilitate access through browsers and hypertext links for future users. This embodiment is similar to that set forth in FIGS. 12A–12C but may proceed independently of and prior to a request for such data. Thus in this embodiment the data translation and collection system 110 may serve to organize and format a patient's records prior to their being requested by a member of the medical staff.

Commencing with FIG. 13A, in step 640 the data translation and collection system 110 receives a data record from a database 106 which may include or be appended to other information specifying patient identification, chronological detail, the data type, and other information regarding the record. In step 644, the data translation and collection system searches each File Format Instruction Table 134 (FIG. 3A) corresponding to each entry in Database Register 131 of Database Table 130 to locate the data type 136 of the received data record. In step 648, the hypertext cipher 138 (FIG. 3B) of File Format Instruction Table 134 may be used to parse the record to identify additional information, such as patient information and the date and time of the record.

In step 650, the system uses the hypertext cipher 138 (FIG. 3B) to determine whether or not the data is stored in a proprietary format. If it is, the applicable proprietary software is used to decompress or translate the data. This may be done on the manufacturer's database 106, another computer processing system, or by the data translation and collection system 110 itself.

In step 654, the record is parsed, discussed infra, to locate data references: hypertext links, multi-media requests, and key words or phrases. If none are found, the process advances to step 682, discussed infra.

If hypertext links or references to other data records are found, they may in steps 664 through 680 be reformatted so that the URL addresses are compatible with addressing protocols used by the hospital. In step 664, the root address 522 of the data record reference 520—which may be in the form of a hypertext link—is extracted as in step 544 (FIG. 12A). Similarly, any descriptors 524—such as patient identification, chronological detail, or other non-addressing information—contained in the data record reference 520 is also extracted and temporarily stored. In step 668, a match for this address root is sought among the Data Request Address Roots 504 (FIG. 10) listed in Data Request Catalogue 500 (FIG. 10), which locates the Database 106 (FIG. 10) and Data Type 136 (FIG. 10) corresponding to the matching Data Request Address Root 504. In step 672, the data type 136 and Database 106 identified in step 668 are cross-referenced with their corresponding File Format Instruction Table 134 (FIG. 3A) to locate the special instructions to request data 142 (FIG. 3B). In step 676, the identified Database 106 and Data Type 136 are referenced in Database Table 130 (FIG. 3A) and the corresponding File Format Instruction Table 134 (FIG. 3B) to acquire the appropriate URL cipher 140 (FIG. 3B). In step 680, the URL cipher 140 processes the descriptors 524—the patient identification, chronological detail, and other information extracted in step 664 to modify or replace the hypertext link or other data reference found in the received data record. Steps 664 through 680 may be performed for each hypertext link and reference to other data records found, in the received data record.

In step 682 the data translation and collection system 110, using the Hypertext Cipher 138, converts any text portion of the selected data record into a browser compatible format, such as HTML format, and any graphics, audio, video, or other non-text information into a browser, plug-in, or Java compatible format.

In step 684, the data translation and collection system 110 inserts hypertext links or other references to the received data record in accordance with the hypertext cipher 138 (FIG. 3B) identified in step 548. If directed by the hypertext cipher 138, the record may also be interpreted and modified or reformatted. In step 686, the URL cipher 140 corresponding to the data type 136 (FIG. 3B) of the received data record processes the descriptors 524—the patient identification, chronological detail, and other information stored or extracted in steps 640 or 648—to format a URL by which the received data record may be accessed.

In step 688, the data translation and collection system 110, having translated and formatted the received data record, forwards the record and its formatted URL to an appropriate database 106 for storage.

Figure 14A:
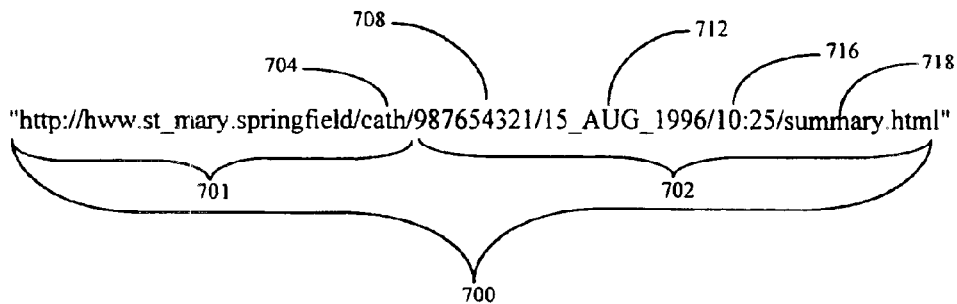
FIGS. 14A–14B are textual representations of a URL address as received and reformatted by the data translation and collection system.

C. Operation of the Hypertext and URL Ciphers of the Data Translation and Collection System FIGS. 14A–14D set forth an example of the hypertext and URL processing performed by the data translation and collection system 110 (FIG. 1) in response to a request for a data record. FIG. 14A proffers, by way of example, a URL address 700 that may be consistent with a standard hospital format, that is received by the data translation and collection system 110.

Embedded in this URL address 700 is information regarding the type of data 704, the patient's identification 708, the date 712 and time 716 of the data requested, and a report designator 718. The type of data 704, combined with additional information, is an example of an address root 701 and the information referred to as 708, 712, 716 and 720 are examples of descriptors 702. The data translation and collection system 110, by following steps 544 through 560 as set forth in FIG. 12A, reformats the data request into a new data request 720 (FIG. 14B), which is compatible with the database system 106 (FIG. 1) holding this data.

Figure 14B:
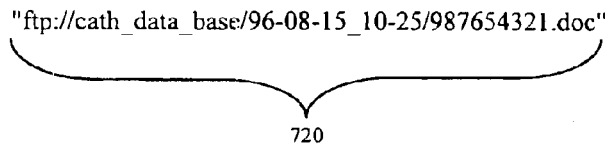
Figure 14C:
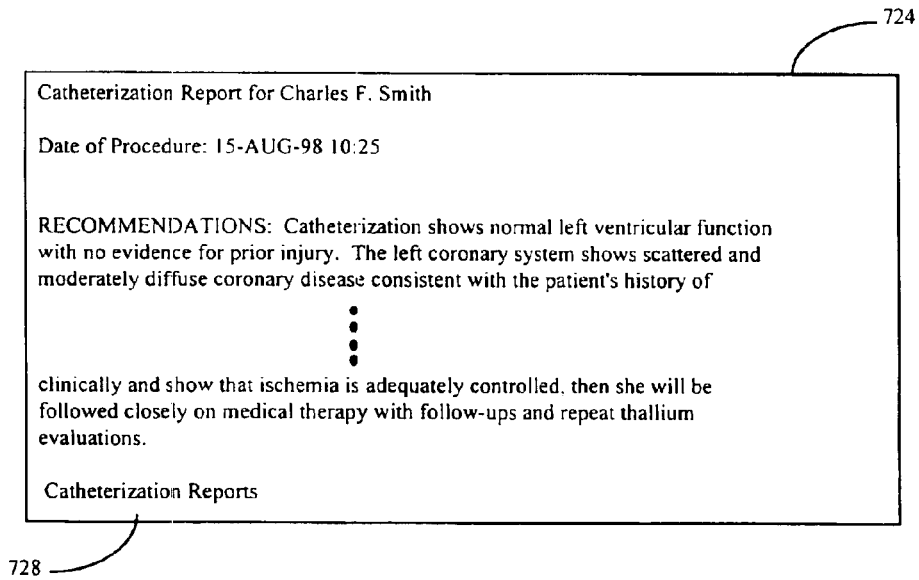
FIG. 14C is a graphical representation of a report referenced by the URL address of FIG. 14B as it would be viewed by a system user through a network browser.

FIG. 14C sets forth an example of a report 724 that may be produced by a database 106 in response to the data request 720 of FIG. 14B. Initially, At the report is only a conventional text document. The data translation and collection system 110 (FIG. 1) may then convert the report into an HTML-compatible format 732 (FIG. 14D), inserting data request 736 and hypertext links 740 and 744 according to the hypertext cipher 138 (FIG. 3B).

The hypertext links 744 may be inserted based upon the recognition of phrases or special character sequences, such as "Catheterization Reports" 728, in the report, which may vary from report to report of the same data type depending on the each report's contents.

Figure 14E:
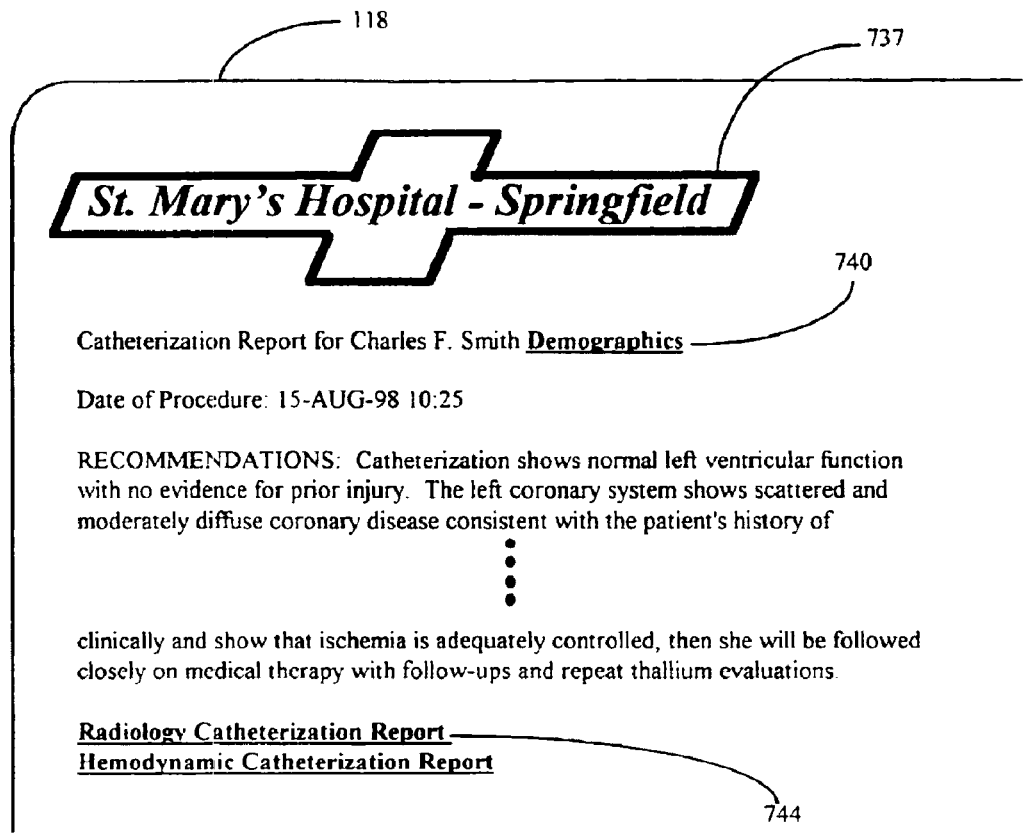
FIG. 14E is a graphical representation of the modified report in FIG. 14D as it would be viewed by a system user through a network browser.

FIG. 14E shows the text report 724 with imported image 737 as displayed on computer display 118 using a network browser software package after the report has been translated and modified. A system user seeking additional information regarding the patient's demographics could select hypertext link 740. A system user seeking either the radiology or hemodynamic report for this procedure could select the appropriate hypertext link 744.

D. Data Collection and Translation for Storage and Retrieval

FIGS. 5A–5E set forth a second alternate embodiment of the operation of the data translation and collection system 110 (FIG. 1) with particular reference to the steps used by the data translation and collection system 110 to retrieve and format data to produce a complete, organized, hypertext-linked, and browser-compatible collection of records pertaining to a person, place, thing, or event. This operation may be initiated by a system user executing the appropriate command or may be executed routinely and automatically by the hospital's Admit, Discharge, and Transfer (ADT) system or Hospital Information System (HIS) during a patient's stay or when a patient is discharged.

In step 200, the data translation and collection system 110 (FIG. 1) receives a patient identification number, which may originate from a staffed workstation 102 (FIG. 1) or automatically from the ADT system 108 (FIG. 1) or HIS 111 (FIG. 1). This may be done, for example, when a patient is admitted or after one has been discharged. In step 204, the data translation and collection system 110 may request the dates for which the system user desires to collect data for the patient or the most recent admission dates from the ADT system 108 or HIS 111. In step 208, a file containing a list of received records will be opened, if previously created, or generated, if not previously created. Similarly, in step 212, a file containing a list of records to be retrieved is opened, if previously created, or generated, if not previously created. In step 216, the data translation and collection system 110 references database table 130 (FIG. 3A) to locate and retrieve the first database entry in the database register 131 (FIG. 3A), the corresponding File Format Instruction table 134 (FIGS. 3A and 3B) and the first data type 136 (FIG. 3B) in the File Format Instruction table 134.

Steps 220 through 276 set forth an iterative search of all the databases 106 (FIG. 1) on the medical computer network 100 (FIG. 1) to collect, translate, and format all records relevant to a patient's medical history.

In step 220, the field containing special instructions to request data 142 (FIG. 3B) corresponding to the data type 136 (FIG. 3B) being referenced by the data translation and collection system 110 is used to construct and format a message which is sent, using address 132 (FIG. 3A), to the database 106 being referenced in database register 131 (FIG. 3A). This message may incorporate passwords, macros, or other codes, as necessary, to retrieve the data. In step 224 a data record is retrieved.

In step 226, the record is parsed per the Hypertext Cipher 138 (FIG. 3B) in the File Format Instruction Table 134 (FIG.

3B) to derive the date and time of the record. In step 228 the file name is added to the list of received records opened in step 208. In step 232, the list of records to retrieve opened in step 212 is checked for a reference to the retrieved record. If a reference exists, in step 236 it is removed from the list of records to retrieve.

In step 240, the system uses the Hypertext Cipher 138 (FIG. 3B) to determine whether or not the data is stored in a proprietary format. If it is, the applicable proprietary software is used to decompress or translate the data. This may be done on the manufacturers database 106, another computer processing system, or by the data translation and collection system 110 itself.

In step 246, the record is parsed, discussed infra, to locate data references: hypertext links, multi-media requests, and key words or phrases. If none are found, the process advances to step 266, discussed infra. If there are data references, a check is made to determine if the data being referenced had been located previously (step 254). If it had not been previously located, the record is added to the List of Records to Retrieve (step 258). In step 262, all hypertext links and other data requests are reformatted through use of the URL Ciphers 140, maintained by the data translation and collection system 110 for each Data Type 136. This is done in a manner similar to steps 580 to 596, discussed supra. Thus when the retrieved data record is later displayed, secondary files referenced by it will be included for display and the system user will not be presented an incomplete record.

In step 266, whether there were data references or not, Hypertext Cipher 138 is used to convert text to HTML format, graphics, audio, video, or other non-text information into a browser, plug-in, or Java compatible format.

While not shown in the flow chart of FIGS. 5A–5E, if the data translation and collection system 110 retrieves a record that includes a program code module such as a Java applet, the data translation and collection system will attempt to retrieve a copy of the applet from an address specified by the applet program code, generate a new address for the applet copy which will be stored with the patient's data record collection, and modify the program code module to reflect the new address. Similarly, if the data translation and collection system 110 retrieves a record that requires a browser extension or "plug-in" in order to be properly viewed, a copy of the applicable extension or "plug-in" is also retrieved for storage with the patient's data record collection.

For purposes of privacy or security, the medical computer network 100 may deny access to some data records in the list of records to be retrieved. In such instances a substitute file, indicating that the requested file is confidential or has not been included, is created and stored, and its reference substituted for the reference to the confidential data record.

In step 268, a retrieved data record may be further modified, such as by inserting additional hypertext links or data requests to the record per the hypertext cipher 138 (FIG. 3B). Also, the URL cipher 140 corresponding to the data type 136 (FIG. 3B) of the retrieved data record is used to format a URL by which the retrieved data record may be accessed. Further, the data translation and collection system 110 creates and opens an appropriate file folder and file to store the converted retrieved record as specified by the URL cipher 140 field.

In step 276, the File Format Instruction Table 134 (FIG. 3B) for the instant database is checked to determine if additional data types 136 are available. If so, in step 272 the process of steps 220 through 276 is repeated for the next data type 136. If the search has been performed for each data a type in the instant database, the search proceeds to the next database indicated in database register 131 (FIG. 3A), starting with its first data type 136 and proceeding, in similar fashion, through each of its data types 136, until the search has been performed for every data type 136 of every database in database table 130 (FIG. 3A). The procedure progresses to step 284 after completing this search through the registered databases.

In step 284, the list of records to retrieve opened in step 212 is examined for the existence of records or program modules that have not yet been retrieved. If the list is empty, the data collection for the patient has been completed and the process advances to step 324 (FIG. 5E), discussed infra. If the list is not empty, in step 288 a request is sent for the first entry remaining in the list, which may be for a data record or a program module. If it is a data record, after it is retrieved, it is checked in step 290 for encryption and decoded, if necessary, using proprietary software.

In step 298, the record is parsed, discussed infra, to locate data references: hypertext links, multi-media requests, and key words or phrases. If none are found, the process advances to step 314, discussed infra. If there are data references a check is made to determine if the data begin referenced had been located previously (step 302). If it had not been previously located, the record is added to the List of Records to Retrieve (step 306). In step 310, all hypertext links and other data requests are reformatted through use of the URL Ciphers 140, maintained by the data translation and collection system 110 for each data type 136. This way, the URL or other data request addresses are compatible with the addressing convention to be used on the storage medium to which the records will be written. When the retrieved data record is later displayed through a network browser, secondary files referenced by the retrieved data record are made easily and quickly accessible to the system user with the click of a mouse.

In step 314, whether there were data references or not, Hypertext Cipher 138 is used to convert text to HTML format, graphics, audio, video, or other non-text information into a browser, plug-in, or Java compatible format.

In step 316, the data translation and collection system 110 creates and opens an appropriate file folder and file to store the converted retrieved record, either as specified by the URL cipher 140 field (FIG. 3B) (if the retrieved record is part of the patient's file), or with a distinctive file name (if the retrieved record is not part of the patient's file, e.g., a physicians biographical background). In step 320, the retrieved record or program module, as it may be, is removed from the list of records to retrieve, and steps 284 through 320 are repeated until the list is empty.

E. Workstation Data Collection and Translation

The operation of the data translation and collection system 110 (FIG. 1) set forth in FIGS. 5A–5E may be initiated in other ways. In one mode of operation, the databases 106 (FIG. 1) on the hospital's communication network 112 may send data for each patient to the data translation and collection system 110 periodically or after the patient is discharged. In another mode of operation, the workstations 102 on the hospital's communication network 112 may send reports, such as those produced by wordprocessors, to the data translation and collection system for translation and storage. In yet another mode of operation, the data translation and collection system may have access to a drive, directory, or folder on one or more of the workstations 102 residing on the communication network, from which it may search and retrieve data records.

System users such as physicians often produce reports, such as word processing files, on their own workstations 102 or 104 (FIG. 1) that are relevant to a patient's condition, status, or profile, and which merit inclusion in the data translation and collection system 110 of the present invention. This need may be accommodated by placing any report that is to be retrieved by the data translation and collection system 110 in a special folder 105 named "Collection." The data translation and collection system 110 may maintain a file containing a Workstation Data Table 150, as set forth in FIG. 4A, which includes the addresses 152 of all workstations 102 and physician office workstations 104 and file access commands 154 or passwords used to gain access to files stored in each workstation's "Collection" folder 105. The data translation and collection system 110 may also maintain a Workstation File Formatting Instruction Table 158, as set forth in FIG. 4B, which includes each report name and corresponding file name and data formatting instructions 162 and Workstation URL cipher 166.

On a periodic basis or as instructed, a program in the data translation and collection system 110 (FIG. 1) may determine if there are any files in the special "Collection" folder 105 in each workstation 102, 104. If any files exist, the file access commands 154 (FIG. 4A) may be sent to the workstation so that the files may be transferred to the data translation and collection system 110. This may be done using the file transfer protocol, FTP, of the Internet/intranet or by other data transfer methods.

If the user of the workstation 102, 104 creates reports, that when stored use a file name formatted according to file name and data formatting instructions 162 (FIG. 4B), the file may be recognized as being a specific file for a patient. For example, the file named "Cath987654321" may correspond to a catheterization report for the patient whose identification number is 987654321. Appending the date and time to the file name may be used to further identify the report. Alternatively, file name and formatting instructions 162 may require that the date and time be located within the report itself. Similarly, the report name and/or the patient's identification information may be incorporated in the report or its file name. In either case, once the file and its file name are received and recognized, the file may be processed in the same manner that data records retrieved from databases are processed as set forth in FIGS. 5A–5E, but using the Workstation Data Table 150 and its Workstation File Formatting Instruction Tables 158 in place of the Database Table 130 and its File Formatting Instruction Tables 134.

Instruments or medical devices whose reports are not stored as part of any database 106 (FIG. 1), but that are capable of writing data to a floppy disk or transmitting information via an infrared or serial line connection to a workstation 102, 104 may also store patient reports in the data translation and collection system 110. To do so, the individual reports may be written to a floppy disk using any file name defined by the file name and data formatting instructions 162 (FIG. 4B). The reports may be copied manually or automatically from the floppy in workstation 102, 104 to the "Collection" folder 105, which may be periodically checked to see if there is any data in it to be retrieved, or the reports may be automatically read by the workstation and sent to the data translation and collection system 110. The reports so sent may be incorporated with any others received for this patient and may be provided with a new destination file according to the Workstation URL Cipher 166.

In this manner reports from wordprocessors or from mobile medical devices may be collected for display and storage and may be assigned structured file names to assist in their retrieval whether on line or when placed on line as with a CD-ROM device 117 (FIG. 2).

F. Creation, Structuring, and Mass-Media Storage of Patient Data

Figure 5A:
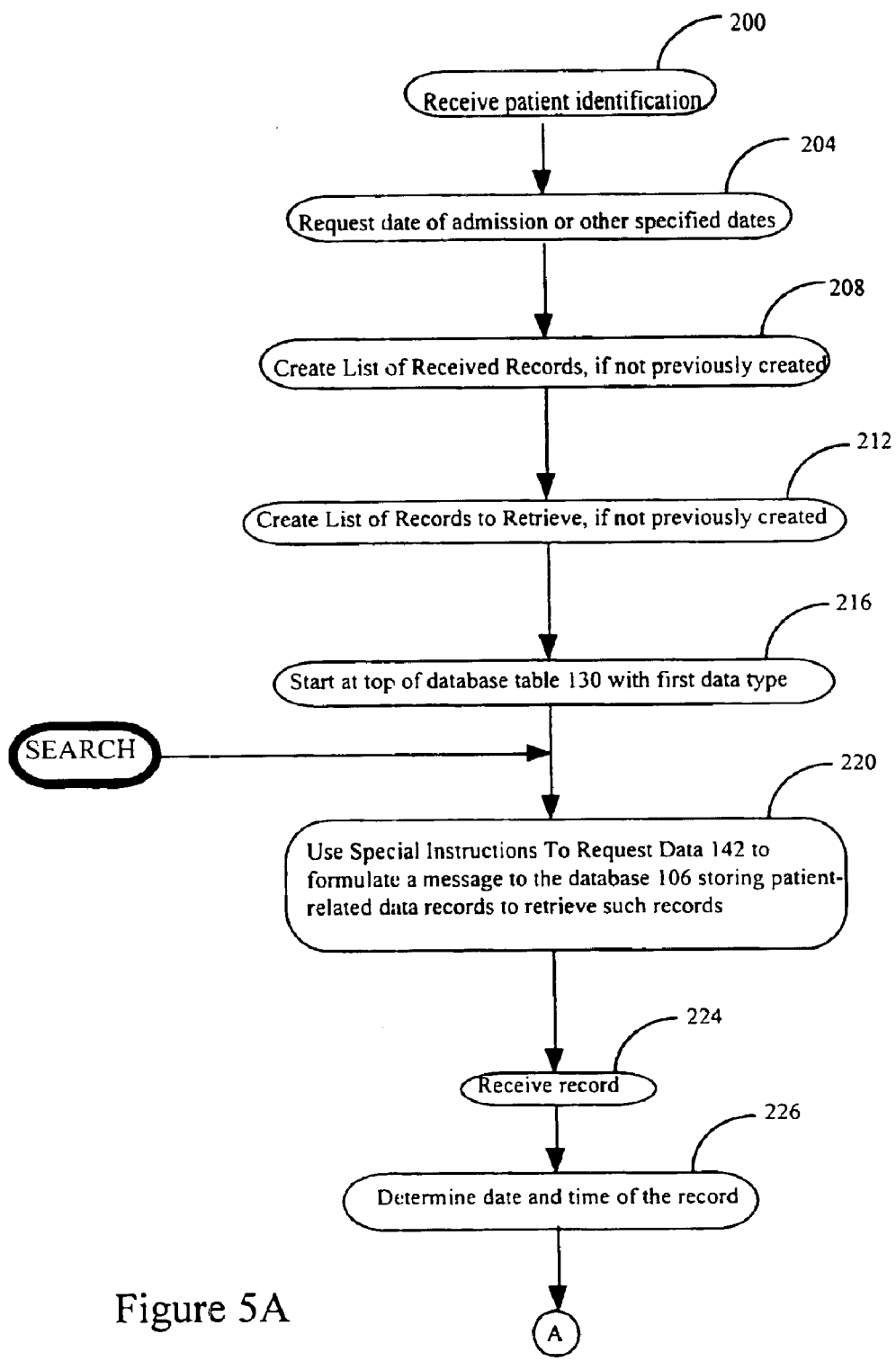
FIGS. 5A–5F are functional flow charts showing the steps used to collect and process a related set of data records from various databases, create a structured set of control files containing hypertext links to the collected data records, and store the data records and control files to a storage device.
Figure 5B:
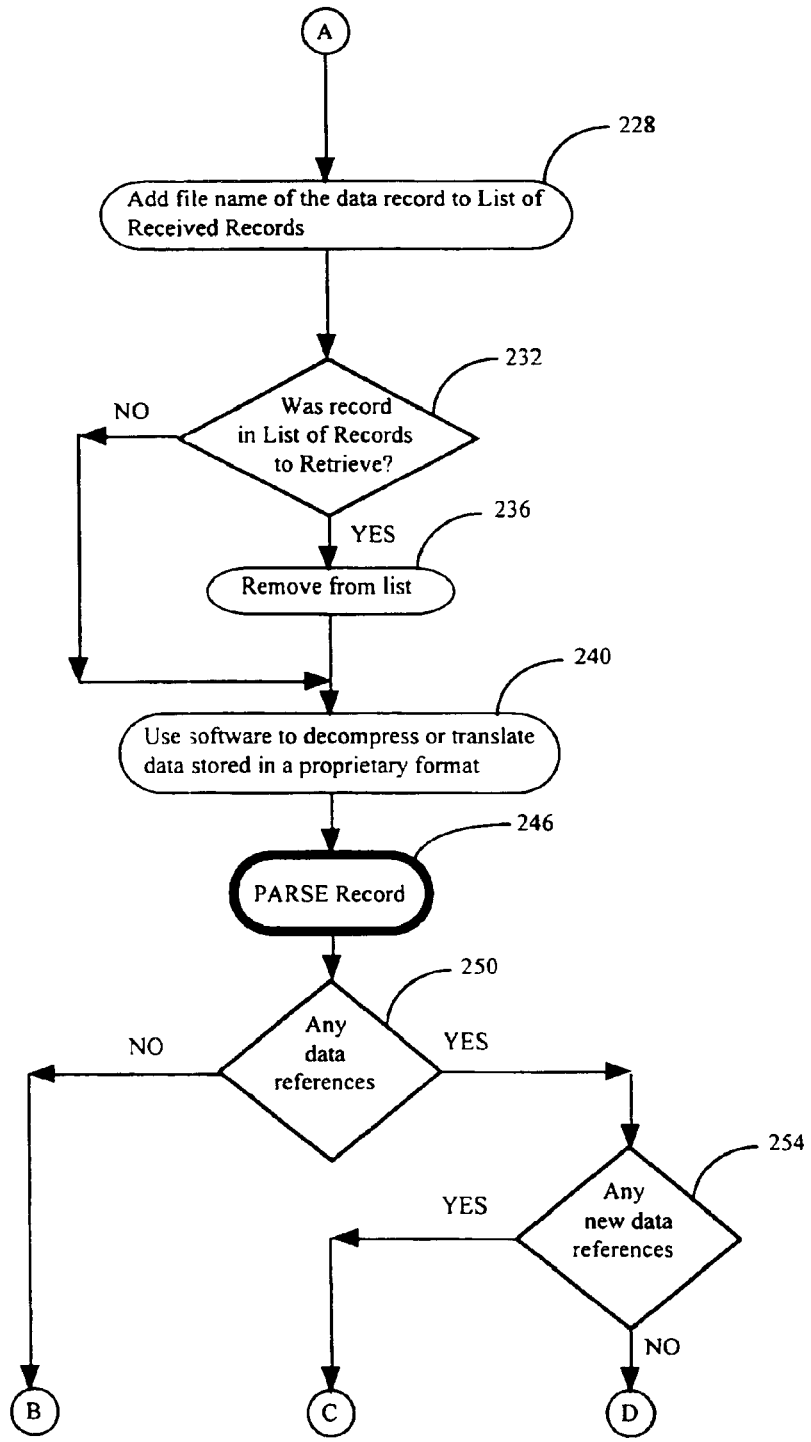
Figure 5C:
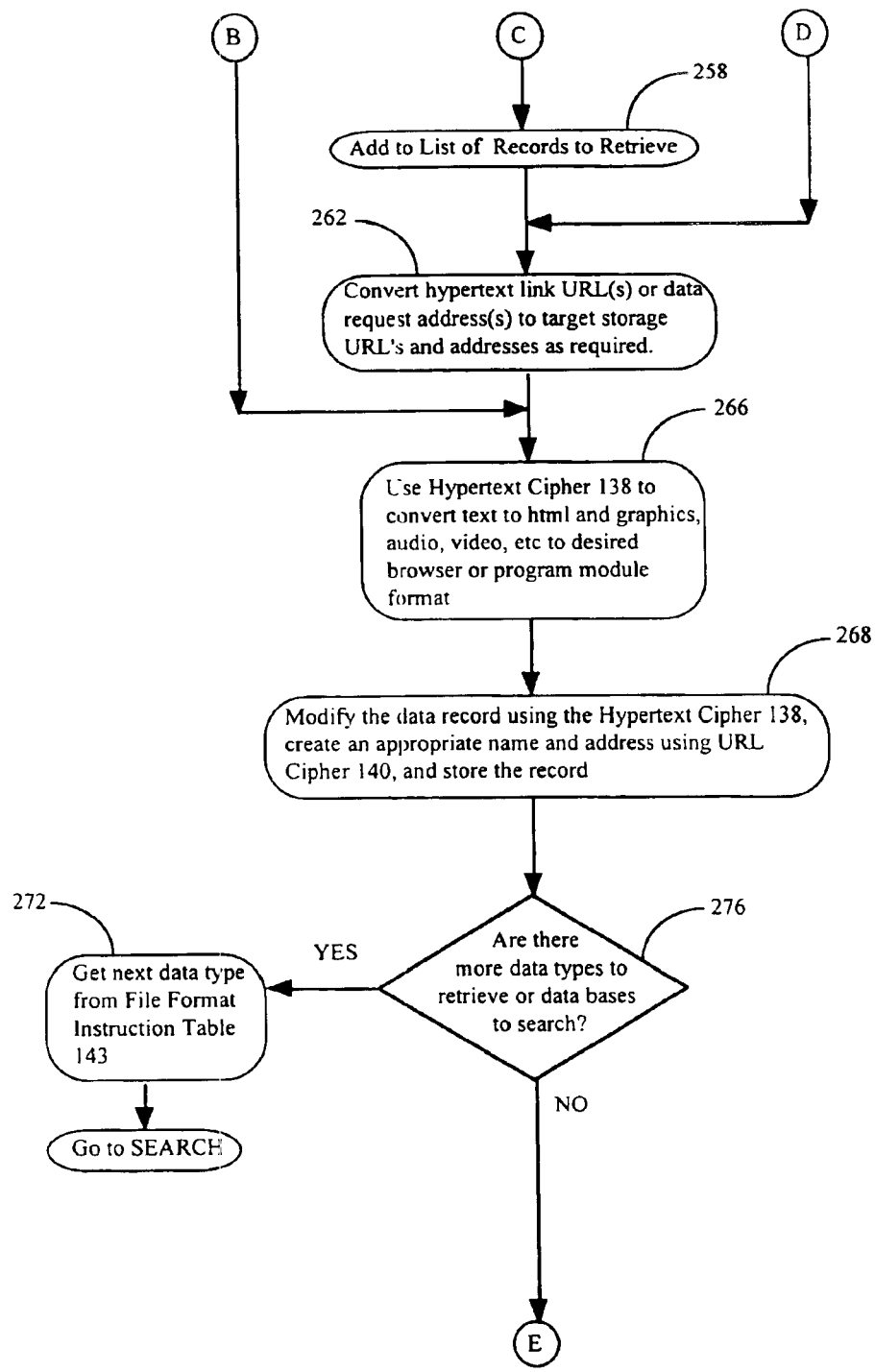
Figure 5D:
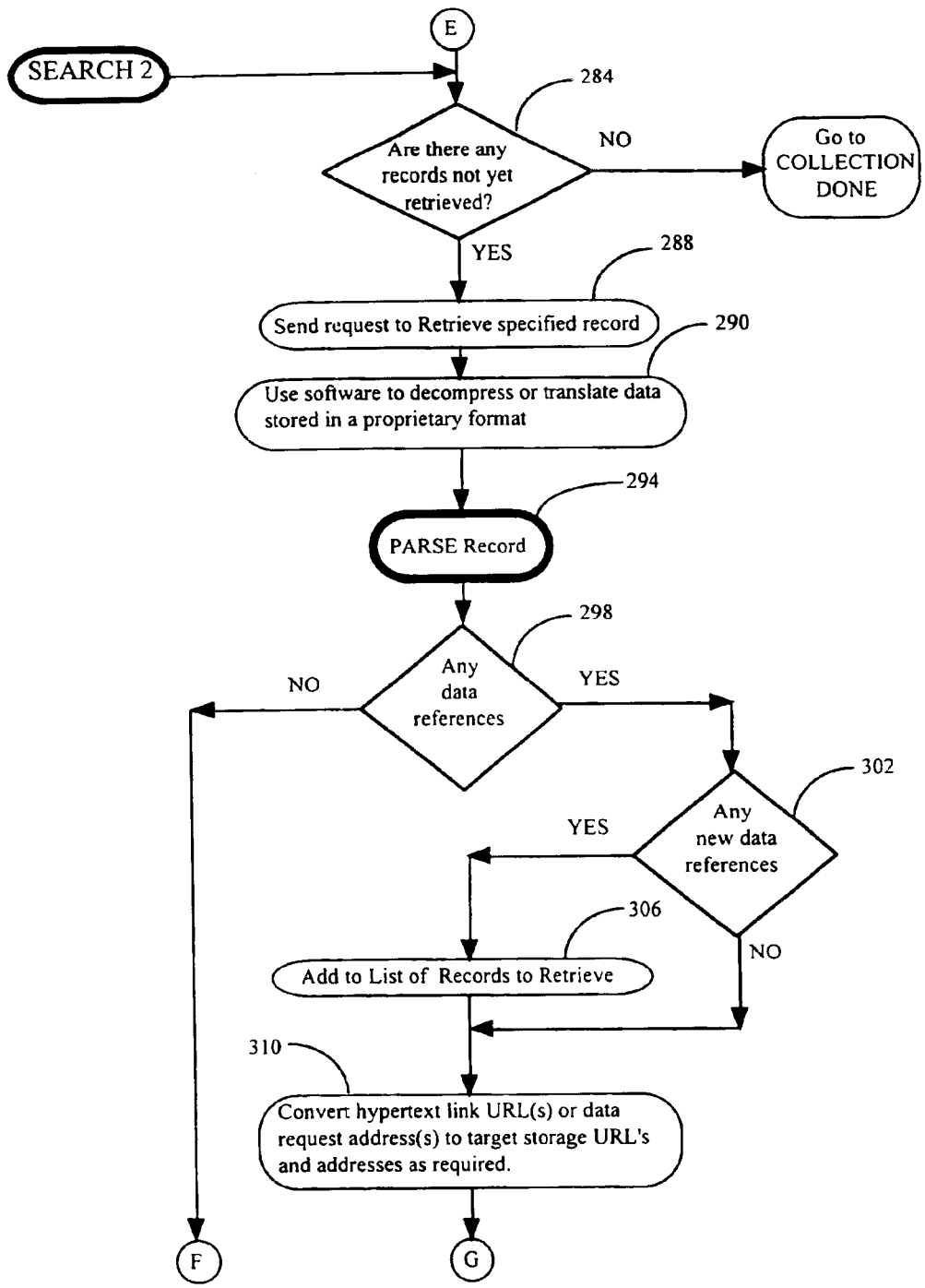
Figure 5E:
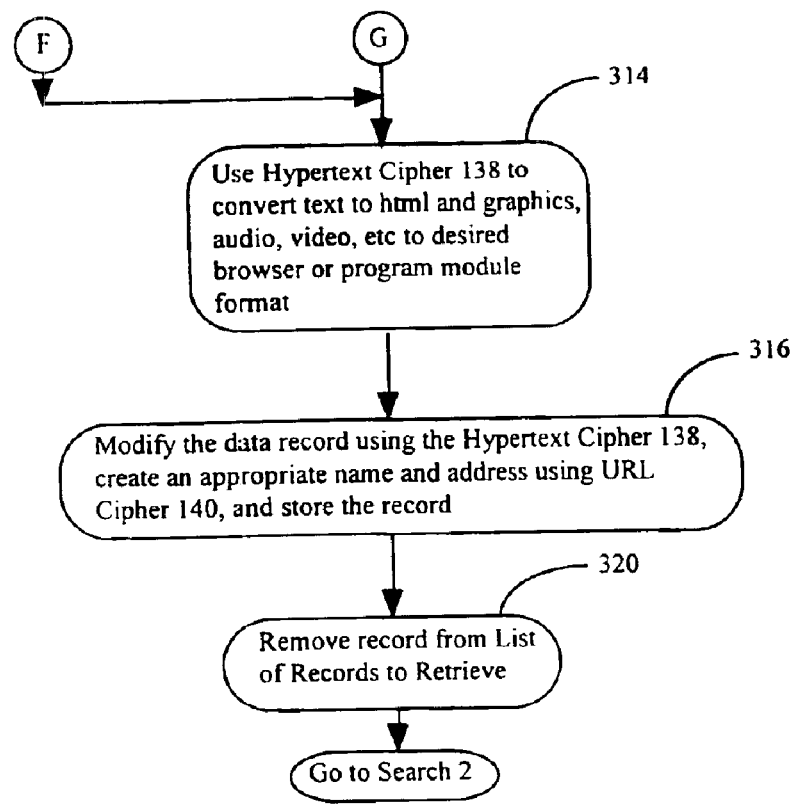
Figure 5F:
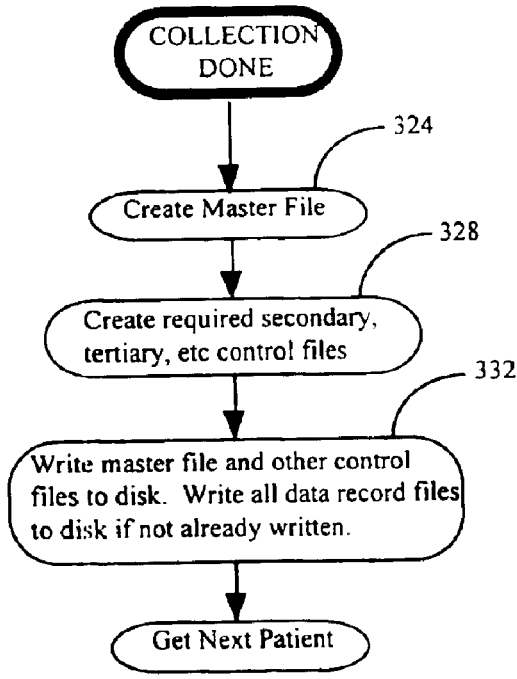

Commencing with step 324, FIG. 5F sets forth the process by which a patient's many data records may be stored on a mass storage device. In step 324, a master file 400 (FIG. 6A) is created as data records are received or when all the data records have been retrieved. The master file name may be based on the patient's name or identification number. In some cases it may be desirable to create the same file twice, using the patient's name for the file name once and the patient's identification number for the other. In step 328, secondary, tertiary, or other subdominant control files 418 (FIG. 8A) may also be created. A "master" file is roughly analogous to a root directory or a home page on a website, for through this single file all the patient's data records may be accessed through hypertext links. While a "master" file may contain text, graphics, video, or audio, it contains a list of links to other reports—for example, the discharge report link 408 (FIG. 6B) to discharge report 412 (FIG. 7A)—or links to other "control" files—for example, the cardiology link 404 to cardiology control file 418 (FIG. 8A). "Control" files are roughly analogous to subdirectories. Although they incorporate text, graphics, or other multimedia features, they serve primarily to present an organized collection of links to related patient records.

The URL Cipher 140 corresponding to the date type 136 of each data record retrieved, can be used to determine whether a hypertext link to retrieve the data record from the mass storage device is to be placed in a master, secondary, or tertiary control file.

In step 332, the master and control files are written to a mass storage device along with the data records if they have not been previously been written to the mass storage device. A CD-ROM disk that has a patient's data written to it may be given to appropriate physicians for their own storage and use. To view the contents of the CD-ROM, a physician would need only to insert it into the CD-ROM drive 117 (FIG. 2) of a physician workstation 104 (FIG. 1) and run a network browser program. By using the File command the physician could refer to the CD-ROM drive 117, which would list the name of the master file 400, which may be the same or similar to the patient's name.

FIG. 6A sets forth an example of the contents of the master file 400. Besides identifying the patient and the dates and source of the medical records, the master file has a series of hypertext links 402 either to distinct reports, such as hypertext link 408, or to secondary control files, such as hypertext link 404. FIG. 6B sets forth how master file 400 (FIG. 6A) might appear through a browser program when presented on display 118. Note that hypertext links 402 are displayed in a different font format, as is the convention with browser programs. The system user may select a hypertext link by moving a pointing device such as a mouse over the text and pressing an activation button. The browser will automatically retrieve the file specified in the hypertext link 402 from the CD-ROM and present it.

If the system user selects the hypertext link 408 specifying discharge report in the master file 400, the system user will be presented with the patient's single discharge report 412 (FIG. 7A). FIG. 7A sets forth some of the HTML codes which may be used to format discharge report 412. Hypertext link 416 may be selected to retrieve the specified catheterization report from the CD-ROM. The hypertext link URL address has been modified as needed to make it compatible with the storage structure of the CD-ROM. FIG. 7B sets forth how discharge report 412 (FIG. 7A) might appear through a browser program when presented on display 118.

FIG. 8A sets forth the contents of a secondary control file 418 that a browser program would present if the system user, while viewing master file 400 (FIG. 6A), selected the hypertext link 404 specifying cardiology data. Secondary control file 418 presents the system user with various types of cardiology reports to choose from in the form of hypertext links 422. For those cardiology tests for which there is only one report available, the hypertext link specifies the URL address of that report. For those tests for which there are several reports available, the hypertext link 420 may specify the URL of a tertiary control file. FIG. 8B sets forth how secondary control file 418 (FIG. 8A) might appear through a browser program when presented on display 118.

FIG. 9A sets forth the contents of tertiary control file 424 that a browser program would present if the system user, while viewing secondary control file 418 (FIG. 8B), selected the hypertext link 420 specifying electrocardiograph reports. This file presents the system user with a list of all the electrocardiograph reports, during the dates selected, to choose from in the form of hypertext links 426. For each electrocardiograph report the hypertext link specifies the URL address of the report. FIG. 9B sets forth how tertiary control file 424 (FIG. 9A) and its list of electrocardiograph reports might appear through a browser program when presented on display 118.

G. Parsing to Locate Data References

Figure 15A:
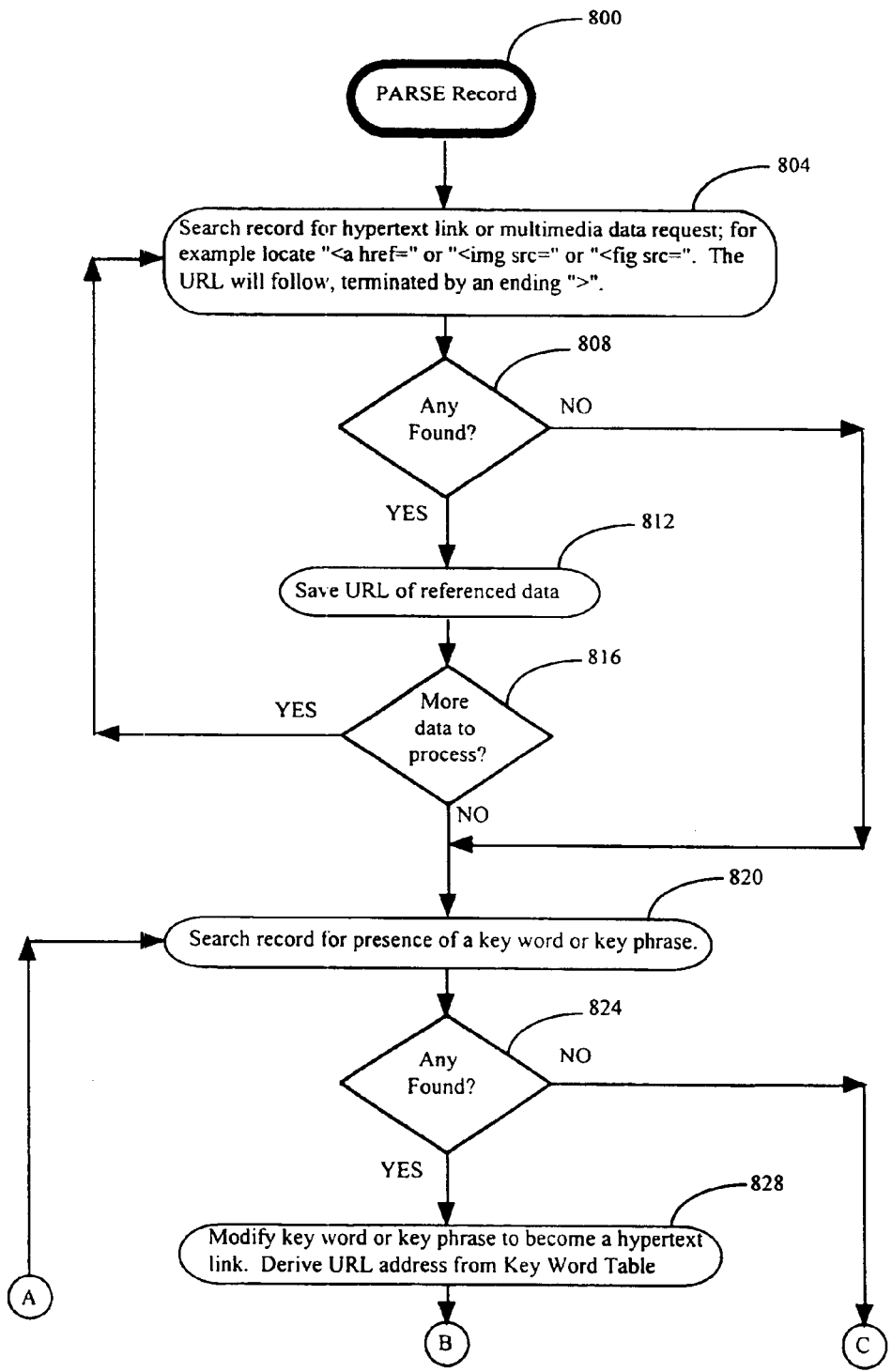
FIGS. 15A–15B are a functional flow chart showing the steps by which a data record is parsed to locate data references within it.
Figure 15B:
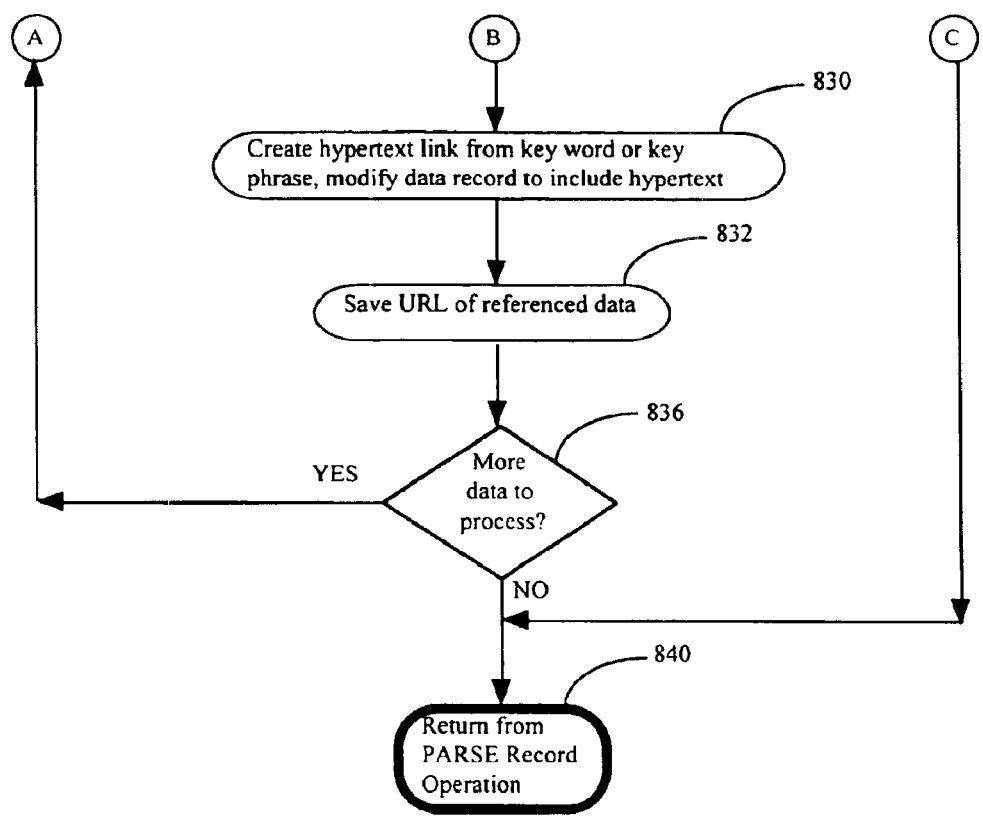

FIG. 15A illustrates how a data record is parsed. A data record is parsed to locate data references by searching it for text corresponding to a hypertext link or a multimedia data request. If one is found, the URL is located after the initial control sequence and will be saved (step 812) for use after the parsing is completed. If none are found, or when the record has been completely parsed, another pass can be made to search for data references in the form of key words or key phrases (step 820).

A key word or phrase is a recognized text string that is to be converted into a hypertext link. As an example, the data reference indicated by the phrase, "Admission ECG," can be converted (steps 828, 830) into the following hypertext link:
<a href="hww.st_mary.springfield/ecg/987654321/
  03may1997/ecg/admission.html">Admission ECG</a>.
The expression "03may1997" is the date the data record being parsed was created. The patient ID (987654321), the date, and other descriptors are available from steps 200 and 226, or from steps 544 or 560. A wide variety of medical expressions can be recognized as key words or phrases, and appropriate hypertext links created from them. The URL of the hyperlink is saved for later use (step 832). When the entire record has been searched (step 836), the URLs of the located data references are returned to the section of the flow chart that requested the record to be parsed (step 840).

H. Building Addresses Using Gleaned Information and Data References in Batch It is contemplated that abbreviated database tables which includes at least some of the information included in database table 130, file format instruction tables 134 (including hypertext ciphers, URL ciphers and special instructions), tables 150 and 158 and data request catalogue 500 can be used to "build" addresses of records referenced in a specific record during batch processing of the specific record (i.e. after the entire first record has been entered).

To this end, referring now to FIG. 21, a first abbreviated database table 1800 preferably includes only data references (DRs) 1802 and associated URL's or address formats 1804. The DRs 1802, like the keywords described above, are searchable terms or phrases which are commonly used to refer to specific occurrences which may be associated with stored records. For example, "admission ecg" may be a DR 1802. Other DRs may include "postop x-ray", "PET image", a date, a patient's identification number, etc. The address formats 1804, like the URL's described above, specify required information needed to form an address of a record associated with the corresponding DR and also specify the sequence of address fields which have to be filled with the required information to form the address.

Referring to FIG. 22, the second abbreviated database table 1820 includes global instructions 1822 and a list of data types 1824 and corresponding record rule sets (RRSs) 1826. The global instructions 1822 include rules for identifying the data type 1824 of a record which is being searched (e.g. to identify key words or phrases for creating links to other records on the system databases 106, 2) in batch form. Different data types 1824 are associated with different record information configurations. For example, one five field record may include a date in the second field while another may include the date in the fourth field. Yet a third record may include the date in the second field but may also include a total of seven fields. These three records would be characterized by three different data types 1824, each different data type 1824 having a different information configuration.

The global instructions 1822 may take any form which, given the data types 1824 used with the wordprocessor 14, can be used to identify a data type 1824. For example, wordprocessor 14 may always provide a single field specifically reserved for a character or symbol which identifies the record data type 1824. For instance, an ecg report may always be entered into a HIS 111 (se FIG. 1) using a first data type template including specific fields for specific information (e.g. patient ID, date, time, physician, etc.). In this case, when an ecg data type template is opened to form an ecg record, wordprocessor 14 automatically enters a "1" in the data type field. Similarly, when a PET scan report is entered into the HIS, assuming PET scan reports are of a second record type, wordprocessor automatically enters a "2" in the data type field.

In the alternative, other global instructions 1822 may specify rules by which wordprocessor 14 can glean information entered by a user into record or template fields to determine the data type. For example, where a user enters a date into a fourth field instead of into a second field, wordprocessor 14 can distinguish a unique data type 1824 or at least a subgroup of data types. Similarly, wordprocessor 14 may recognize specific terms entered into certain fields to identify data type 1824. For example, when a user enters "ecg" into a first field, wordprocessor 14 may recognize a specific data type based on global instructions 1822. While only two different examples of global instruction have been described herein, the examples are not meant to be exhaustive and other examples are contemplated.

Referring still to FIG. 22, the data types 1824 correspond to the different field configurations of the various record which are stored on the in the system databases 106, 2. The RRSs 1826 each include a set of rules for gleaning information from a record which is being searched (e.g. to identify key words or phrases for creating links to other records on the system databases 106, 2). For example, where DT-1 1828 indicates a first record type having five fields including a first patient ID field, a second date field, a third report type field, a fourth physician name field and a fifth text field, the corresponding RRS-1 1830 includes rules which specify that to glean the patient ID, date, report type and physician name, wordprocessor 14 must access the first, second, third and fourth fields, respectively.

Figure 16:
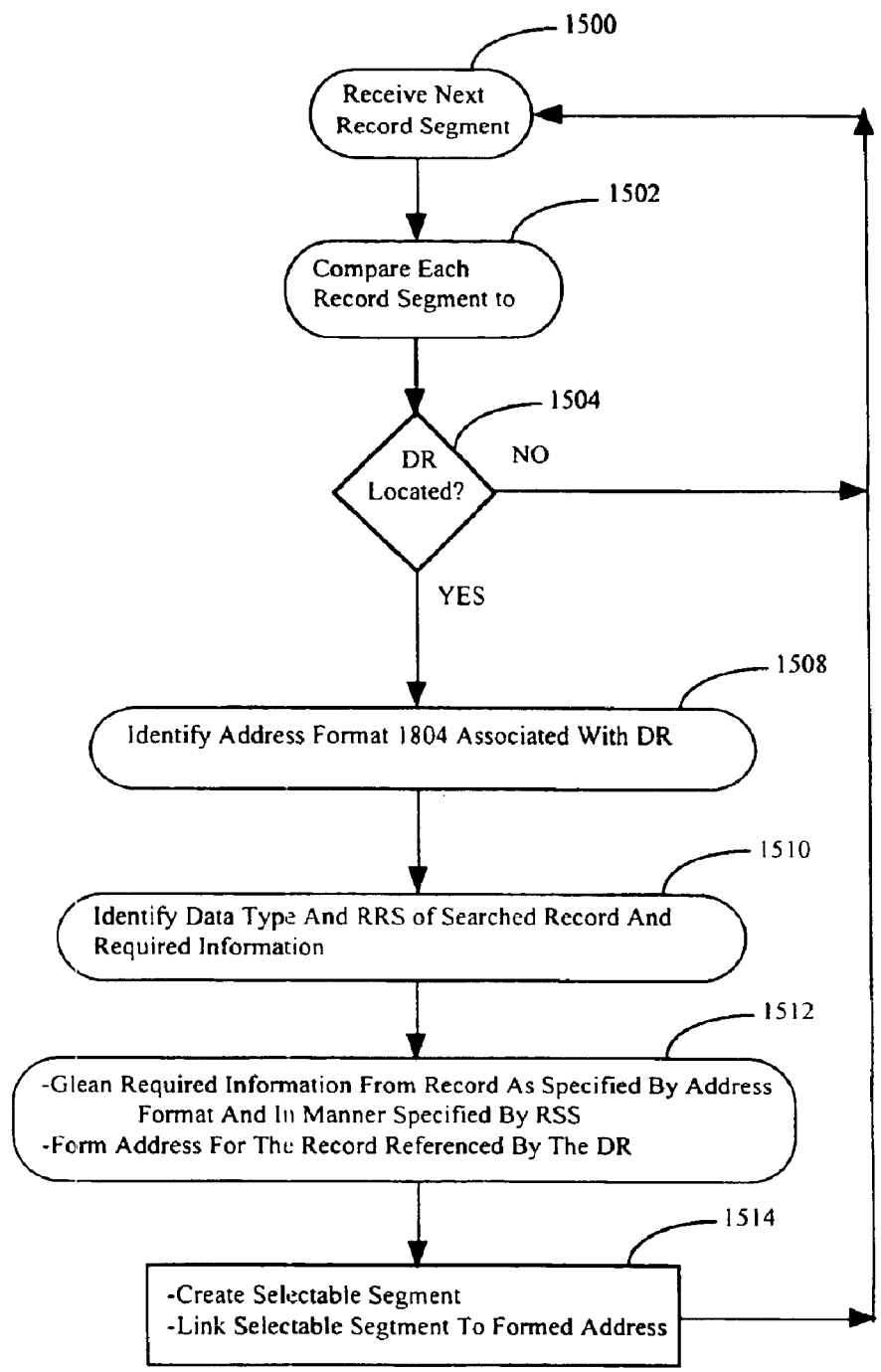
FIG. 16 is a flow chart illustrating a method of forming or building record addresses using a record rule set and an address format in real time according to the present invention.

Referring now to FIG. 16, a batch method performed by wordprocessor 14 (see also FIG. 1) is illustrated. The method of FIG. 16 will be described in the context of an exemplary process. To this end, it will be assumed that a plurality of records have already been stored at database addresses according to the methods described above and in accordance with the specifications of the tables of FIGS. 21 and 22. Thus, each of the stored records is associated with a DR 1802 and is stored at a database address which has a format indicated by an associated address format 1804 in the table of FIG. 21. For example, a record associated with DR-3 1808 is stored at an address having a format consistent with Format 3 1810. Records which have already been stored will be referred to generally as first records.

In addition, referring also to FIG. 17, it will be assumed that the record illustrated therein (hereinafter a "second record") has been entered into the HIS and stored on one of the system databases 106, 2. The record in FIG. 17 is a report created using wordprocessor 14. The record includes DRs 1608 which reference a plurality of the first data records. Initially it is contemplated that DRs 1608 would not be highlighted but that, after wordprocessor 14 forms links between DRs 1608 and records corresponding to the DRs 1608, the DRs 1608 would be highlighted via bolding or a different color text. In FIG. 17 the DRs 1608 include "admission ecg," "previous ecg," "previous discharge cath," and "admission CK enzyme" referencing various stored first records.

For each of the DRs 1608 (i.e. keywords) in FIG. 17, wordprocessor 14 is capable of recognizing these DRs and correlating the DRs with address formats 1804 via table 1800. In addition, wordprocessor 14 is also capable of determining the data type 1828 of the record shown in FIG. 17 and an associated RRS 1826 using the global instructions 1822 from table 1820.

For the purposes of this explanation it will be assumed that the data type 1824 for the record illustrated in FIG. 17 includes five fields. In addition to a text field 1607, the four other fields include a patient ID field 1600, a date field 1602, a report type field 1604 and an author field 1606. It is also assumed that each of fields 1600, 1602, 1604, 1606 and 1607 already includes the information illustrated in FIG. 17.

In addition, the record of FIG. 17 also includes a data type field 1610. In the present example, it is assumed that, at an earlier time, when a physician accesses wordprocessor 14 to create a record, the physician indicates the data type to the wordprocessor in some manner. Data type may be indicated by selecting a data type from a list (e.g. ecg, PET report, post op X-ray, etc.) or it may be typed or it may be indicated in any other manner. When the physician indicates a data type 1824, word processor 14 places a character or a character string in data type field 1610 indicating the data type of the record being created. In addition, wordprocessor 14 thereafter can provide fields to be filled in which are consistent with the specified data type 1824. In this case, it is assumed that "DT-1" indicates an admission report having fields 1600, 1602, 1604, 1606, 1607 and 1610.

With the second record completed as illustrated in FIG. 17 and stored on one of the system databases 106, 2, a command is issued to wordprocessor 14 to search the second record to identify any references to first records which occur in the second record and, when a reference to a first record is located, to form a link between the reference and the referenced first record. To this end, wordprocessor 14 performs the process of FIG. 16. Wordprocessor 14 separately receives each phrase in field 1607 (where the phrases include groupings of N or less consecutive words where N is the maximum number of consecutive words which may be included in a DR 1802), and compares each phrase to DRs 1802 in table 1800 to identify DRs 1802. Where a phrase does not match a DR 1802, wordprocessor 14 jumps to the next entered phrase.

Referring to FIGS. 16 and 17, when the phrase "admission ecg" is received as a second record segment at step 1500, at step 1502 wordprocessor 14 accesses table 1800 and compares the phrase "admission ecg" to the DRs 1802 until either a match is identified or until the phrase has been compared to all of the DRs 1802. In the alternative, table 1800 entries may be stored alphabetically and wordprocessor 14 may be equipped to recognize the first letter in a phrase. In this case, wordprocessor 14 may compare the phrase only to DRs 1802 which begin with the first letter of the phrase being compared to speed up the comparison process. At decision block 1504, where the phrase does not match a DR 1802, control passes back to processes step 1500 where the next record phrase or segment is received for comparison.

However, at block 1504, where the phrase matches a DR 1802, control passes to block 1508. In the present example it will be assumed that DR-3 1808 corresponds to the phrase "admission ecg". Thus, the phrase "admission ecg" matches a DR-3 1808 and control passes to block 1508. At block 1508 wordprocessor 14 uses table 1800 to identify address format (i.e. URL cipher) 1810 which corresponding to ORs 1808. As indicated above, the address format specifies a format of an address associated with DR-3 1808 and also specifies the required information needed to form the record address.

Next, at process block 1510, wordprocessor 14 accesses the global instructions 1822 in table 1820 and uses the rules therein to determine the data type 1824 of the second record. In the present example, the global instructions 1822 instruct the wordprocessor to access data type field 1610 to identify the data type 1824. Accessing field 1610, wordprocessor 14 determines that the second record data type is DT-1. Accessing table 1824, wordprocessor 14 correlates data type DT-1 1828 with RRS-1 1830. As indicated above, RRS-1 1830 specifies rules for how to glean the required information from the record illustrated in FIG. 17. For example, address format 1810 may require, among other information, a patient ID number and a date used to locate reports for a particular patient related to the date. In the present example, RRS-1 1830 may specify that the information in field 1600 corresponds to a patient ID and that the information in field 1602 corresponds to the current date.

Now using RRS-1 1830, at process block 1512, wordprocessor 14 gleans the required information as specified by address format 1810 from the second record in the manner specified by RRS-1 1830. To this end, in the present example, wordprocessor 14 gleans the patient ID number and the date from fields 1600 and 1602.

Next, at block 1512, wordprocessor 14 forms an address for the record referenced by DR-3 1808. At block 1514 wordprocessor 14 automatically highlights the DR 1608 "admission ecg" in text field 1607 thus providing the DR "admission ecg" as a selectable segment. In addition, wordprocessor 14 links the DR "admission ecg" to the formed address such that, when the DR "admission ecg" is selected (e.g. via a mouse controlled cursor or the like), the wordprocessor 14 automatically accesses the record stored at the formed address and provides the record to a user for review.

In addition to information facially included in the second record, wordprocessor 14 may also glean other information associated with the second record for building a record address. For example, wordprocessor 14 may be associated with a specific facility and therefore may associate every record generated by the wordprocessor 14 with the specific facility (i.e. St. Mary's Springfield). In this case, when gleaning information, wordprocessor 14 may also glean information specifying the specific facility which is required to form an address. This information may be gleaned from any of a variety of locations including admit system 108, hospital information system 11 or some other system linked to a hospital database 106, 2.

This process of comparing record segments to DRs 1802 and forming links between DRs 1802 and records referenced by the DRs 1802 is continued on the second record text. In the present example links are formed between phrases (i.e. DRs 1802) "previous discharge cath" and "admission CK enzyme" and records referenced thereby. For example, the address linked to the phrase "admission ecg" is identified by number 1700 while the address linked to the phrase "previous discharge ecg" is identified by number 1702.

In addition, information in fields 1600 through 1606 may also be recognizable DRs 1802. In this case wordprocessor 14 also forms links between information in those fields and corresponding records by first determining if the information in a field is a DR 1802, identifying the address format 1804 corresponding to the DR 1802, identifying required information for forming an address, identifying a data type 1824 corresponding to the record being searched, identifying the RRS 1826 associated with the data type 1824, gleaning the required information as indicated by the RRS 1826, forming an address for the record referenced by the DR 1802 by combining the required information, providing the DR 1802 as a selectable segment and linking the selectable segment to the record via the formed address. For example, the address linked to the patient ID number and associated patient demographics is identified by number 1704 and the address linked to the staff directory information for Dr. Markelson is identified by number 1706.

Referring now to FIG. 18 therein is illustrated an HTML document corresponding to the document of FIG. 17 including hypertext addresses formed according to the process of FIG. 16. It can be seen that each of the DRs 1608 of FIG. 17 now includes a linking address.

Referring also to FIG. 19, the document of FIG. 18 is illustrated as the document would be viewed via wordprocessor 14 or a standard network browser (not illustrated). As illustrated, six selectable segments have been Ad highlighted (i.e. underlined), a separate selectable segment for each recognized DR.

It should be noted that while the above-referenced batch processing to build record addresses has been described in the context of the wordprocessor 14, some other data translation and collection system (e.g. 110 in FIG. 1) may be provided to perform exactly the same functions in batch format.

It should also be noted that while specific fields may be provided in a record template for entering specific types of information, in another embodiment, a single field may be able to receive more than one type of information from which a wordprocessor or other type of device could glean the separate types of information for building a record address. For example, in one embodiment, a patient's ID number, a date, a time and perhaps other information may be provided in a single field, the wordprocessor 14 able to parse information in the single field to identify specific types of information. In this case, it is contemplated that there would have to be rules to avoid duplication of specific types of information in the single field. For example, there would have to be a rule that no more than one patient ID could be provided in the field or that, if more than a single patient ID were provided in the field, one of the ID numbers would have to be selected for generating an address.

In yet another embodiment of the present invention, referring to FIGS. 21, 22 and 23, portions of the data in tables 21 and 22 are combined to form even a more abbreviated database table 1900 which can be used to form database addresses for DRs which reference a first record in a second record. To this end, table 1900 includes a data reference (DR) list 1902, and both address formats 1904 and record rule sets (RRSs) 1906 which are correlated with the DRs 1902. In this embodiment the DR list 1902 and address formats 1904 have the same purposes and forms as the list in FIG. 21.

However, instead of being linked to a second record type, a separate RRS 1906 is linked to each of the unique DRs 1902. In this case, each RRS 1906 includes a set of rules which, independent of a second record's data type, indicate how to glean required information for forming a record address form the second record information. For example, a particular medical facility may require a patient ID be identified as "ID:_" followed by a 9 digit number. In this case, the RRSs 1906 would specify that the term "ID:_" followed by a 9 digit number is a patient identification which can be used to populate a patient ID field in an address format. Similarly, the RRSs 1906 in this example include other rules which can be used to glean information from a second record for forming an address.

Referring to FIG. 16, the method illustrated therein would be essentially the same using the table of FIG. 23 instead of the tables of FIGS. 21 and 22 and therefore, the method using table 1900 will not be explained here in detail. The only difference in the method of FIG. 16 when using table 1900 is that, at process block 1510, the wordprocessor does not have to identify the data type and identifies the RRS by correlating the RRS with the DR in table 1900.

I. Real Time Operation of Address Building Using Ciphers

U.S. patent application Ser. No. 08/727,293 which was filed on Oct. 9, 1996 and is entitled "Method and System for Automated Data Storage and Retrieval with Uniform Addressing Scheme" is incorporated herein by reference. That application teaches a system whereby, as record information is entered into a record, a wordprocessor analyzes the information in real time to identify keywords, roots or data references (DRs) which are references to other records which are stored or which may be subsequently stored on one of the system databases 106, 2. It is contemplated that the abbreviated database tables illustrated in FIGS. 21 and 22 can be used to "build" addresses of records referenced in a specific record as the record is entered into a wordprocessor database 2. Thus, the process of forming record addresses described above in the context of batch processing (i.e. processing after the records have already been entered and stored) can be practiced in real time.

To this end, referring again to FIG. 16, the wordprocessor method illustrated therein can also be performed in real time. To describe real time operation of the wordprocessor 14 to generate links between records, once again, it will be assumed that a plurality of records have already been stored at database addresses according to the methods described above and in accordance with the specifications of the tables of FIGS. 21 and 22. Thus, each of the stored records is associated with a DR 1802 and a corresponding data type 1828 and address format 140 1804. Records which have already been stored will be referred to generally as first records. In addition, referring also to FIG. 17, it will be assumed that the second record illustrated therein is being entered into the database 2 in real time.

For each of the ORs 1802 (i.e. keywords), wordprocessor 14 is capable of recognizing these DRs 1802 in the document illustrated in FIG. 17 and correlating the DRs 1802 with address formats 1804 via table 1800. In addition, wordprocessor 14 is also capable of determining the data type 1828 of the record shown in FIG. 17 as that record is being input in real time and an associated RRS 1826 using the global instructions 1822 from table 1820.

As in the batch example above, the record of FIG. 17 includes a data type field 1610. In the present example, it is assumed that, when a physician initially accesses wordprocessor 14 to create the record of FIG. 17, the physician indicates the data type to the wordprocessor in some manner. For example, data type may be indicated by selecting a data type from a list (e.g. ecg, PET report, post op X-ray, etc.). When the physician indicates a data type 1824, word processor 14 places a character or a character string in data type field 1610 indicating the data type of the record being created. In addition, wordprocessor 14 thereafter can provide fields to be filled which are consistent with the specified data type 1824. Once again, it is assumed that "DT-1" indicates an admission report having fields 1600,1602, 1604, 1606, 1607 and 1610.

After fields 1600 through 1606 are filled, the physician is prompted to enter report text into field 1607. During text entry, wordprocessor 14 performs the process of FIG. 16. To this end, processor 14 receives each phrase entered into field 1607 (where the phrases include groupings of N or less consecutive words where N is the maximum number of consecutive words which may be included in a DR 1802), and compares each phrase to DRs 1802 in table 1800 to identify DRs 1802. Where a phrase does not match a DR 1802, wordprocessor 14 jumps to the next entered phrase.

Referring to FIGS. 16 and 17, when the phrase "admission ecg" is received as a second record segment at step 1500, at step 1502 wordprocessor 14 accesses table 1800 and compares the phrase "admission ecg" to the DRs 1802 until either a match is identified or until the phrase has been compared to all of the DRs 1802. At decision block 1504, where the phrase does not match a DR 1802, control passes back to processes step 1500 where the next record phrase or segment is received for comparison.

However, at block 1504, where the phrase matches a DR 1802, control passes to block 1508. In the present example it will again be assumed that DR-3 1808 corresponds to the phrase "admission ecg". Thus, the phrase "admission ecg" matches a DR-3 1808 and control passes to block 1508. At block 1508 wordprocessor 14 uses table 1800 to identify address format (i.e. URL cipher) 1810 which corresponding to DRs 1808. As indicated above, the address format specifies a format of an address associated with DR-3 1808 and also specifies the required information needed to form the record address.

Next, at process block 1510, wordprocessor 14 accesses the global instructions 1822 in table 1820 and uses the rules therein to determine the Next, at process block 1510, wordprocessor 14 accesses the global instructions 1822 in table 1820 and uses the rules therein to determine the data type 1824 of the second record. In the present example, the global instructions 1822 instruct the wordprocessor to access data type field 1610 to identify the data type 1824. Accessing field 1610, wordprocessor 14 determines that the second record data type is DT-1. Accessing table 1824, wordprocessor 14 correlates data type DT-1 1828 with RRS-1 1830. As indicated above, RRS-1 1830 specifies rules for how to glean the required information from the record illustrated in FIG. 17. For example, address format 1810 may require, among other information, a patient ID number and a date used to locate reports for a particular patient related to the date. In the present example, RRS-1 1830 may specify that the information in field 1600 corresponds to a patient ID and that the information in field 1602 corresponds to the current date.

Now using RRS-1 1830, at process block 1512, wordprocessor 14 gleans the required information as specified by address format 1810 from the second record in the manner specified by RRS-1 1830. To this end, in the present example, wordprocessor 14 gleans the patient ID number and the date from fields 1600 and 1602.

Next, at block 1512, wordprocessor 14 forms an address for the record referenced by DR-3 1808. At block 1514 wordprocessor 14 automatically highlights the DR 1608 "admission ecg" in text field 1607 thus providing the DR "admission ecg" as a selectable segment. In addition, wordprocessor 14 links the DR "admission ecg" to the formed address such that, when the DR "admission ecg" is selected (e.g. via a mouse controlled cursor or the like), the wordprocessor 14 automatically accesses the record stored at the formed address and provides the record to a user for review.

This process of comparing record segments to DRs 1802 and forming links between DRs 1802 and records referenced by the DRs 1802 is continued as text is entered into the record text field 1607. In the present example links are formed between phrases (i.e. DRs 1802) "previous discharge cath" and "admission CK enzyme" and records referenced thereby.

In addition, as in the batch example above, information in fields 1600 through 1606 may also be recognizable DRs 1802. Here, the only difference in wordprocessor 14 operation is that the DRs in fields 1600–1606 are recognized as the fields are filled and, if all of the required information is not yet entered for building an address, the wordprocessor 14 waits to build the address until all of the required information has been provided. For example, referring still to FIGS. 17 and 21, where the patient ID field 1600 is recognized as a DR 1802 and the date in field 1602 is required to form an address to a record corresponding to the patient and the date, if the date has not yet been entered, the wordprocessor 14 must wait for the date to be entered prior to forming the address. In the alternative, the wordprocessor 14 may be programmed to wait until all fields 1600–1606 are filled prior to building any addresses for DRs (i.e. processing of information in the preliminary, non-text fields may be done in batch):

It should be understood that while the real time addressing method described above is described in the context of the tables of FIGS. 21 and 22, the table of FIG. 23 may be used instead, the only differences being that in step 1510 wordprocessor 14 does not identify the second record data-type and that the wordprocessor 14 determines the RRS by correlating an RRS 1906 in table 1900 with an identified DR 1902.

While a particular embodiment of the invention has been illustrated and described, it will be obvious to those skilled in the art that various changes and modifications may be made without sacrificing the advantages provided by the principle of construction disclosed herein. For example, while the present invention has been described above in the context of an interface wherein a physician enters record information via a keyboard, clearly the invention is not to be so limited. For example, data may be dictated into a system, the inventive wordprocessor including voice recognition software and identifying DRS as they are dictated and forming links between the DRS and records referenced thereby.

Figure 20:
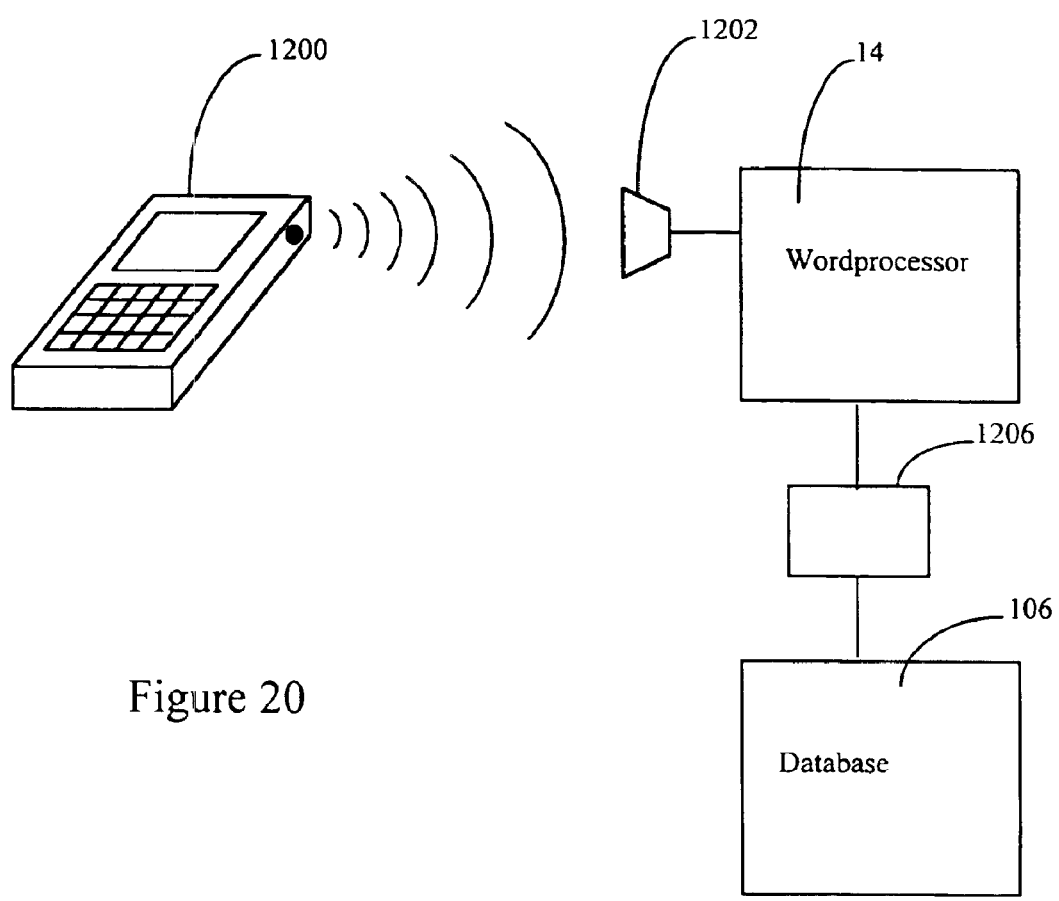
FIG. 20 is a schematic of specifying devices and a processor of the present invention.

In the alternative, referring to FIG. 20, the system may be used with a data specifying device such as a hand held information gathering device (HHD) 1200 which downloads record information via a receiver (e.g. rf) 1202 which is entitled "Data Collection Device and System", which is commonly owned with the present application and which is incorporated herein by reference. In this type of system, the HHD may in fact specify a DR which can be used by processor to identify a DB address in any of several different ways. For example, processor 14 may simply correlate the DR with a DB address. In the alternative, processor 14 may build an address using the DR and an associated address format. In addition to specifying the DR, it is also contemplated that the HHD specifies other information for forming the DB address (e.g. background or general data set information such as patient ID, time, date, etc.). Also, it should be recognized that any data specifying device may be used such as a database which indicates a DR or the like. To this end, see the DB 106 linked to processor 14 via a network router 1206 or other network device (i.e. a receiver) in FIG. 20.

Furthermore, it should be recognized that the present invention may also be used in the case of a proxy server which routes address commands and requests among network devices. For example, the invention may build record addresses which do not actually match record addresses on a database but which, when provided to a proxy server, enable the proxy server to identify the actual record addresses and form a link.

To apprise the public of the scope of this invention, we make the following claims.

What is claimed is:

1. A system for linking first record references to a first record wherein the references are in a second record, the system comprising:
   (a) a database (DB) including:
   at least one address format specifying an address format of the first record address; and
   (b) a processor linked to the DB and running a pulse sequencing program to perform the steps of:
   (i) receiving the second record;
   (ii) analyzing the second record to identify references to the first record; and
   (iii) when a first record reference is identified, using information from the second record to form the address of the first record as specified by the address format.

2. The system of claim 1 wherein the address format also specifies required information for forming the address for the first record, the DB further includes at least one record rule set (RRS) specifying rules for gleaning the required information from a record and, wherein, when the first record is referenced in the second record, the processor gleans the required information from the second record in the manner specified by the RRS.

3. The system of claim 2 wherein the RRS corresponds to the address format.

4. The system of claim 2 wherein the second record is characterized by a data type, the RRS is associated with the data type and the processor, prior to gleaning, determines the second record data type and identifies the RRS associated with the second record data type.

5. The system of claim 2 wherein the DB also includes a data reference (DR) which is associated with the address format and wherein, when searching for a reference to the first record, the processor searches for instances of the DR.

6. The system of claim 5 wherein the program includes a wordprocessor, the DR is a text name associated with the first record and the first record address is a markup language data reference.

7. The system of claim 1 also for creating markup language data references between the first record references and the first record, the processor also, when a first record reference is identified, provides the first record reference to a user as a selectable segment and links the selectable segment to the first record via the first record address such that, when the selectable segment is selected, the first record is provided to the user.

8. The system of claim 7 further including a processor wherein, after the selectable segment is provided, the processor performs the steps of, when the second record is accessed, monitoring changes to the second record and, when the selectable segment is modified, de-links the selectable segment and the first record.

9. The system of claim 5 wherein the DB includes a plurality of address formats and their associated RRSs and DRs, and, wherein the processor searches the second record for any of the DRs and, when any of the DRs is identified, the processor identifies the associated address format and RRS, gleans the required information from the second record in the manner specified by the associated RRS and forms the address corresponding to the first record.

10. The system of claim 1 further including an interface for entering the second record, the second record entered in record segments and, wherein, the processor runs the program as second record segments are entered via the interface.

11. The system of claim 1 for use with a data specifying device wherein the step of receiving includes receiving the second record from the data specifying device.

12. A system which receives database records, each record including a separate information set and characterized by at least one data type, for a specific record, the system using the specific record's information set to construct a record address which enables easy subsequent record access, the system comprising:
   (a) a database (DB) including at least one address format which is associated with the at least one record type and which specifies a unique set of required information to form a record address for the record type; and
   (b) a processor linked to the DB and running a pulse sequencing program to perform the steps of, for the specific record:
   (i) receiving the information set;
   (ii) confirming the data type and the associated address format;
   (iii) analyzing the information set to glean the required information;
   (iv) using the required information to form a record address as specified by the address format; and
   (v) storing the record at the record address.

13. The system of claim 12 wherein there are a plurality of record types, the DB includes a separate address format for each of the different record types and, wherein, the step of confirming includes the steps of determining the record type and the associated address format.

14. The system of claim 12 wherein the DB further includes at least a separate record rule set (RRS) specifying a set of rules for gleaning required information from a record and, wherein, the processor gleans required information in the manner specified by the RRS.

15. The system of claim 14 wherein the RRSs correspond to each of the address formats.

16. The system of claim 15 wherein the program is a first application program and the processor also performs a second application program to link stored records which are referenced in a first record to the referenced records, to this end the processor further performing the steps of, after at least one record is stored:
searching the first record for a reference to a stored record;
when a reference to a stored record is identified:
determining the address associated with the referenced record;
providing the reference to a user as a selectable segment and linking
the selectable segment to the referenced stored record via the record address such that, when the selectable segment is selected, the record is provided to the user.

17. The system of claim 16 wherein the processor provides a data reference (DR) for the record information set, the DR useable of refer to the record in other records, the processor, when searching for a reference in the first record, searching for the DR.

18. The system of claim 17 wherein, after the record address is formed, the processor also correlates the DR with the record address and stores the DR along with the record address, the processor determining the address associated with a reference by identifying the address associated with an identified DR.

19. The system of claim 17 wherein the RRS is a first RRS and the DB also associates a second RRS with the address format, the second RRS specifying rules for gleaning the required information from the first record, when a DR is gleaned from an information set, the processor also correlating the DR with the address format and storing the DR along with the address format, the processor determining the address associated with a reference by, when a DR is identified:
identifying the address format associated with the DR;
identifying the second RRS associated with the identified address format and the required information specified by the identified address format;
gleaning the required information from the first record as specified by the second RRS; and
forming the record address using the required information and as specified by the address format.

20. A method of collecting a group of related data records on a computer system and storing said data records in a manner permitting their retrieval in an ordered manner and display by an interactive display program capable of displaying a plurality of interface supported data formats, comprising:
(a) receiving a first reference to a group of related data records from an accessory computer system;
(b) retrieving said group of related data records using information in said first reference, a list of databases and a list of instructions for retrieving each data record;
(c) creating a reference to each of said related data records;
(d) creating a master control file; and
(e) storing said group of related data records and said master control files to a data storage device.

21. The method of claim 20 wherein the step of creating a master control file includes also creating a plurality of secondary control files, prior to storing, the method further including the step of determining in which of said master control or secondary control file said reference is to be placed by using information in a list of data types and the step of storing including storing the group of related data records and the master control and secondary control files to a data storage device.

22. A system which receives database records, each record including a separate information set and characterized by at least one data type, for a specific record, the system using the specific record's information set to identify a record address which enables easy subsequent record access, the system also for use with a data specifying device which provides the database records, including at least one field specifying a data reference, the system comprising:
a receiver for receiving records from the specifying device; and
a processor linked to the receiver and running a pulse sequencing program to perform the steps of, for a specific record:
(i) receiving the information set;
(ii) identifying the DR;
(iii) using the DR to identify a record address for the record; and
(iv) storing the record at the record address.

23. The system of claim 22 wherein the specifying device is a hand held device.

24. The system of claim 22 wherein the specifying device is a database.

25. The system of claim 22 wherein the specifying device, in addition to specifying the DR, also specifies other information which is used to identify the address.

26. A method for linking first record references to a first record wherein the references are in a second record, the method used with a database (DB) including at least one address format specifying an address format of the first record address, the method comprising the steps of:
(i) receiving the second record;
(ii) analyzing the second record to identify references to the first record; and
(iii) when a first record reference is identified, using information from the second record to form the address of the first record as specified by the address format.

27. The method of claim 26 wherein the address format also specifies required information for forming the address for the first record, the DB further includes at least one record rule set (RRS) specifying rules for gleaning the required information from a record and, wherein, the method further includes the steps of:
when the first record is referenced in the second record, gleaning the required information from the second record in the manner specified by the RRS.

28. The method of claim 27 wherein the RRS corresponds to the address format and, wherein, prior to gleaning, the method includes the step of correlating the RRS with the address format to identify the RRS.

29. The method of claim 27 wherein the second record is characterized by a data type, the RRS is associated with the data type and, prior to gleaning, the method includes the steps of determining the second record data type and identifying the RRS associated with the second record data type.

30. The method of claim 27 wherein the DB also includes a data reference (DR) which is associated with the address format and wherein the step of searching includes searching for instances of the DR.

31. The method of claim 26 also for creating markup language data references between the first record references and the first record, the method further including the steps of:
when a first record reference is identified, providing the first record reference to a user as a selectable segment; and
linking the selectable segment to the first record via the first record address such that, when the selectable segment is selected, the first record is provided to the user.

32. The method of claim 31 wherein, after the selectable segment is provided, the method includes the steps of, when the second record is accessed, monitoring changes to the second record and, when the selectable segment is modified, de-linking the selectable segment and the first record.

33. The method of claim 29 wherein the DB includes a plurality of address formats and their associated RRSs and DRs, and, wherein the step of searching includes searching the second record for any of the DRs and, when any of the DRs is identified, the method includes the steps of identifying the associated address format and RRS, gleaning the required information from the second record in the manner specified by the associated RRS and forming the address corresponding to the first record.

34. The method of claim 26 further including an interface for entering the second record, the second record entered in record segments and, wherein, the method is performed as second record segments are entered via the interface.

35. The method of claim 26 for use with a data specifying device wherein the step of receiving includes receiving the second record from the data specifying device.

36. A method which receives database records, each record including a separate information set and characterized by at least one data type, for a specific record, the method using the specific record's information set to construct a record address which enables easy subsequent record access, the method for use with a database including at least one address format which is associated with the at least one record type and which specifies a unique set of required information to form a record address for the record type, the method comprising the steps of:
(i) receiving the information set;
(ii) confirming the data type and the associated address format;
(iii) analyzing the information set to glean the required information;
(iv) using the required information to form a record address as specified by the address format; and
(v) storing the record at the record address.

37. The method of claim 36 wherein there are a plurality of record types, the DB includes a separate address format for each of the different record types and, wherein, the step of confirming includes the steps of determining the record type and the associated address format.

38. The method of claim 37 wherein the DB further includes at least a separate record rule set (RRS) specifying a set of rules for gleaning required information from a record and, wherein, the step of gleaning includes gleaning the required information in the manner specified by the RRS.

39. The method of claim 38 wherein the RRSs correspond to each of the address formats.

40. The method of claim 39 wherein the method also links stored records which are referenced in a first record to the referenced records, to this end the method further including the steps of, after at least one record is stored:
searching the first record for a reference to a stored record;
when a reference to a stored record is identified:
determining the address associated with the referenced record;
providing the reference to a user as a selectable segment and linking the selectable segment to the referenced stored record via the record address such that, when the selectable segment is selected, the record is provided to the user.

41. The method of claim 40 wherein the database includes a data reference (DR) for the record information set, the DR useable of refer to the record in other records and the method includes the steps of, when searching for a reference in the first record, searching for the DR.

42. The method of claim 41 wherein, after the record address is formed, the method also includes the steps of, correlating the DR with the record address and storing the DR along with the record address, the method determining the address associated with a reference by identifying the address associated with an identified DR.

43. The method of claim 41 wherein the RRS is a first RRS and the DB also associates a second RRS with the address format, the second RRS specifying rules for gleaning the required information from the first record, when a DR is gleaned from an information set, the method also correlating the DR with the address format and storing the DR along with the address format, the method determining the address associated with a reference by, when a DR is identified:
identifying the address format associated with the DR;
identifying the second RRS associated with the identified address format and the required information specified by the identified address format;
gleaning the required information from the first record as specified by the second RRS; and
forming the record address using the required information and as specified by the address format.

* * * * *